US008388604B2

(12) United States Patent
Kassab

(10) Patent No.: US 8,388,604 B2
(45) Date of Patent: Mar. 5, 2013

(54) DEVICES, SYSTEMS, AND METHODS FOR REMOVING CONTRAST FROM LUMINAL ORGANS

(75) Inventor: Ghassan S. Kassab, Zionsville, IN (US)

(73) Assignee: DTherapeutics, LLC, Zionsville, IN (US)

(*) Notice: Subject to any disclaimer, the term of this patent is extended or adjusted under 35 U.S.C. 154(b) by 357 days.

(21) Appl. No.: 12/714,218

(22) Filed: Feb. 26, 2010

(65) Prior Publication Data
US 2010/0174271 A1    Jul. 8, 2010

Related U.S. Application Data

(60) Continuation-in-part of application No. 11/891,981, filed on Aug. 14, 2007, now Pat. No. 8,114,143, which is a division of application No. 10/782,149, filed on Feb. 19, 2004, now Pat. No. 7,454,244.

(60) Provisional application No. 60/449,266, filed on Feb. 21, 2003, provisional application No. 60/493,145, filed on Aug. 7, 2003, provisional application No. 60/502,139, filed on Sep. 11, 2003.

(51) Int. Cl.
| A61M 1/00 | (2006.01) |
| A61M 29/00 | (2006.01) |
| A61B 6/00 | (2006.01) |
| A61B 5/04 | (2006.01) |

(52) U.S. Cl. .... 604/540; 604/35; 604/96.01; 604/99.01; 604/119; 600/431; 600/547

(58) Field of Classification Search ............... 604/35, 604/96.01, 99.01, 119, 540
See application file for complete search history.

(56) References Cited

U.S. PATENT DOCUMENTS

| 3,896,373 A | 7/1975 | Zelby |
| 4,380,237 A | 4/1983 | Newbower |
| 4,587,975 A | 5/1986 | Salo |
| 4,840,182 A | 6/1989 | Carlson |
| 4,957,110 A | 9/1990 | Vogel et al. |
| 5,058,583 A | 10/1991 | Geddes et al. |
| 5,125,410 A | 6/1992 | Misono et al. |
| 5,233,994 A | 8/1993 | Shmulewitz |
| 5,366,443 A | 11/1994 | Eggers et al. |

(Continued)

FOREIGN PATENT DOCUMENTS

| EP | 1 025 805 A1 | 8/2000 |
| WO | WO 98/35611 A1 | 8/1998 |

(Continued)

OTHER PUBLICATIONS

PCT/US2010/031553, PCT International Preliminary Report on Patentability, dated Oct. 18, 2011.

(Continued)

*Primary Examiner* — Jackie Ho
*Assistant Examiner* — Joshua Lee
(74) *Attorney, Agent, or Firm* — Ice Miller LLP

(57) ABSTRACT

Devices, systems, and methods for removing contrast from luminal organs. In at least one embodiment of a device for removing contrast from luminal organs of the present disclosure, the device comprises an elongated body having at least one lumen extending therethrough and an aperture defined along the elongated body, said aperture configured to facilitate withdrawal of contrast from a mammalian luminal organ, a first detector for detecting a contrast present within the mammalian luminal organ, the detector positioned at or near a distal end of the elongated body, an inflatable balloon coupled to the elongated body proximal to the detector, and a second detector for detecting balloon inflation, the second detector positioned along the elongated body within the balloon.

27 Claims, 14 Drawing Sheets

U.S. PATENT DOCUMENTS

| | | | |
|---|---|---|---|
| 5,453,576 | A | 9/1995 | Krivitski |
| 5,665,103 | A | 9/1997 | Lafontaine et al. |
| 5,827,192 | A | 10/1998 | Gopakumaran et al. |
| 5,842,998 | A | 12/1998 | Gopakumaran et al. |
| 5,971,933 | A | 10/1999 | Schlueter et al. |
| 6,112,115 | A | 8/2000 | Feldman et al. |
| 6,165,977 | A | 12/2000 | Mochly-Rosen |
| 6,187,744 | B1 | 2/2001 | Rooney |
| 6,191,136 | B1 | 2/2001 | Marban |
| 6,270,493 | B1 | 8/2001 | Lalonde et al. |
| 6,296,615 | B1 | 10/2001 | Brockway et al. |
| 6,325,762 | B1 | 12/2001 | Tjin |
| 6,354,999 | B1 | 3/2002 | Dgany et al. |
| 6,360,123 | B1 | 3/2002 | Kimchi et al. |
| 6,471,656 | B1 | 10/2002 | Shalman et al. |
| 6,494,832 | B1 | 12/2002 | Feldman et al. |
| 6,511,413 | B2 | 1/2003 | Landesberg |
| 6,545,678 | B1 | 4/2003 | Ohazama |
| 6,569,862 | B1 | 5/2003 | Marban |
| 6,663,661 | B2 | 12/2003 | Boneau |
| 6,666,828 | B2 | 12/2003 | Greco et al. |
| 6,926,674 | B2 | 8/2005 | Tenerz et al. |
| 7,069,072 | B2 | 6/2006 | Jansen et al. |
| 7,141,019 | B2 | 11/2006 | Pearlman |
| 7,169,107 | B2 | 1/2007 | Jersey-Willuhn et al. |
| 7,189,208 | B1 | 3/2007 | Beatty et al. |
| 7,211,073 | B2 * | 5/2007 | Fitzgerald ............... 604/500 |
| 7,236,820 | B2 | 6/2007 | Mabary et al. |
| 7,311,702 | B2 | 12/2007 | Tallarida et al. |
| 7,326,241 | B2 | 2/2008 | Jang |
| 2002/0049488 | A1 | 4/2002 | Boneau |
| 2002/0091349 | A1* | 7/2002 | Reich ..................... 604/5.01 |
| 2002/0099254 | A1* | 7/2002 | Movahed .................. 600/4 |
| 2003/0013986 | A1 | 1/2003 | Saadat |
| 2004/0024329 | A1 | 2/2004 | Jansen et al. |
| 2004/0044286 | A1 | 3/2004 | Hossack et al. |
| 2004/0116816 | A1 | 6/2004 | Tenerz et al. |
| 2006/0013772 | A1* | 1/2006 | LeWinter et al. ......... 424/9.52 |
| 2007/0161914 | A1 | 7/2007 | Zdeblick et al. |
| 2008/0176271 | A1 | 7/2008 | Silver et al. |
| 2008/0194996 | A1 | 8/2008 | Kassab |
| 2008/0269581 | A1 | 10/2008 | Wood et al. |
| 2009/0216133 | A1 | 8/2009 | Kassab |
| 2010/0041984 | A1 | 2/2010 | Shapeland et al. |

FOREIGN PATENT DOCUMENTS

| | | |
|---|---|---|
| WO | WO 02/19905 | 3/2002 |
| WO | WO 02/085442 A1 | 10/2002 |
| WO | WO 03/092495 A1 | 11/2003 |

OTHER PUBLICATIONS

PCT/US2010/032178, PCT International Preliminary Report on Patentability, dated Nov. 3, 2011.

PCT/US04/04828, PCT Search Report and Written Opinion dated Jul. 6, 2005.

Hoekstein and Inbar, "Cardiac Stroke Volume Estimation from Two Electrodes Electrical Impedance Measurements." Technion Department of Electrical Engineering Publication EE PUB No. 911, Feb. 1994.

L. Kornet, J.R.C. Jansen, E.J. Gussenhoven, M.R. Hardeman A.P.G. Hoeks and A. Versprille, "Conductance Method for the Measurement of Cross-Sectional Areas of the Aorta," Annals of Biomedical Engineering, vol. 27, pp. 141-150, 1999.

Douglas A. Hettrick, Joseph Battocletti, James Ackmann, and David C. Warltier, "Finite Element Model Determination of Correction Factors Used for Measurement of Aorta Diameter via Conductance," Annals of Biomedical Engineering, vol. 27, pp. 151-159, 1999.

Douglas A. Hettrick, Joseph Battocletti, James Ackmann, John Linehan, and David C. Warltier, "In Vivo Measurement of Real-Time Aortic Segmental Volume Using the Conductance Catheter," Annals of Biomedical Engineering, vol. 26, pp. 431-440, 1998.

PCT/US06/05985, PCT Search Report and Written Opinion dated Aug. 8, 2007.

Supplementary European Search Report for EP Application Serial No. EP 04 71 2383 to Electro-Cat, LLC, dated Aug. 6, 2007.

International Searching Authority, International Search Report, mailed Aug. 16, 2012 (PCT/US2011/023911).

International Searching Authority, Written opinion of the International Searching Authority, mailed Aug. 16, 2012 (PCT/US2011/023911).

International Searching Authority, International Search Report, mailed Aug. 30, 2012 (PCT/US2011/024961).

International Searching Authority, Written opinion of the International Searching Authority, mailed Aug. 30, 2012 (PCT/US2011/024961).

International Searching Authority, International Search Report, mailed Sep. 7, 2012 (PCT/US2011/026337).

International Searching Authority, Written opinion of the International Searching Authority, mailed Sep. 7, 2012 (PCT/US2011/026337).

* cited by examiner

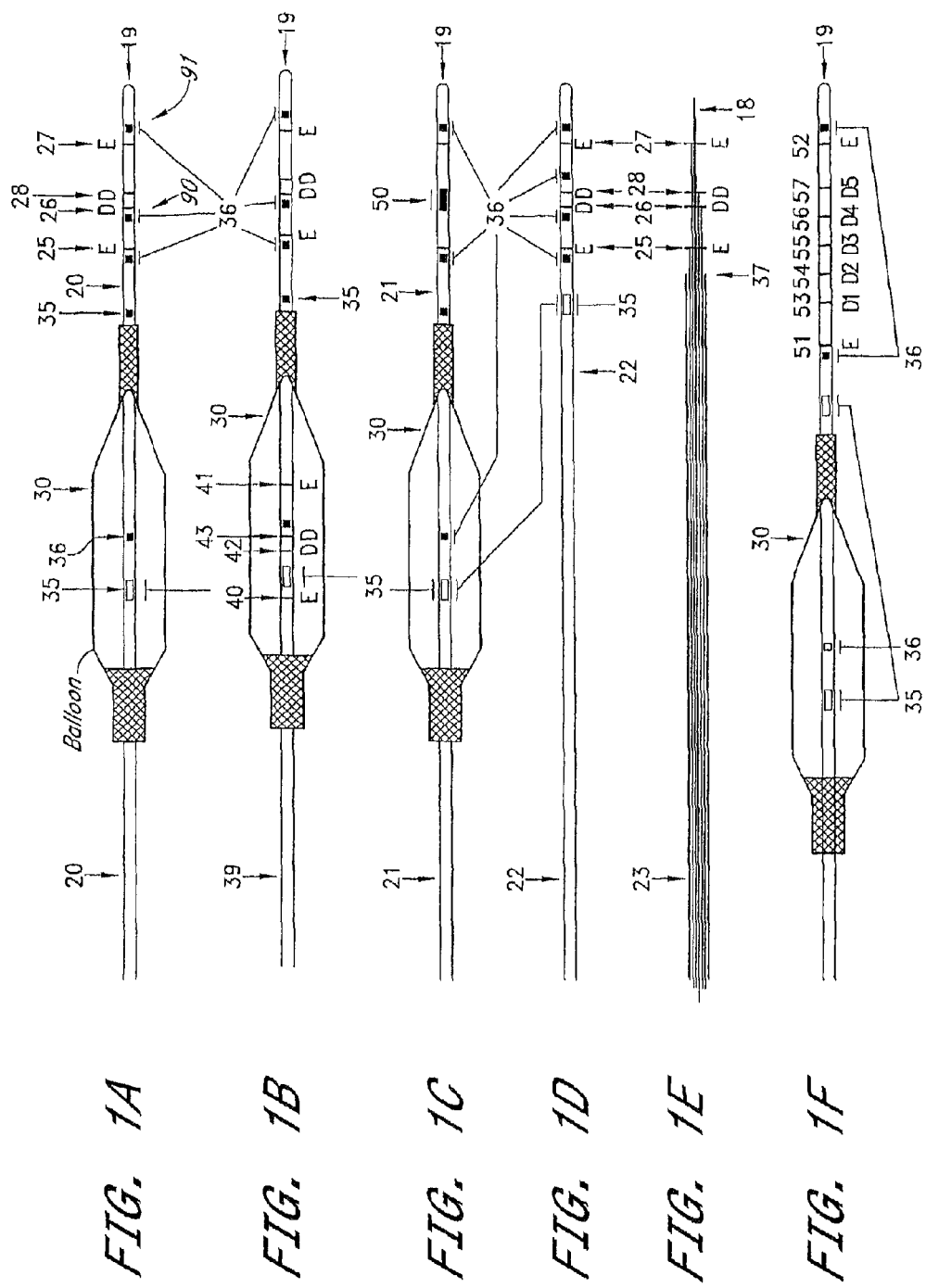

envelope data peak-peak of voltage at the detection electrodes

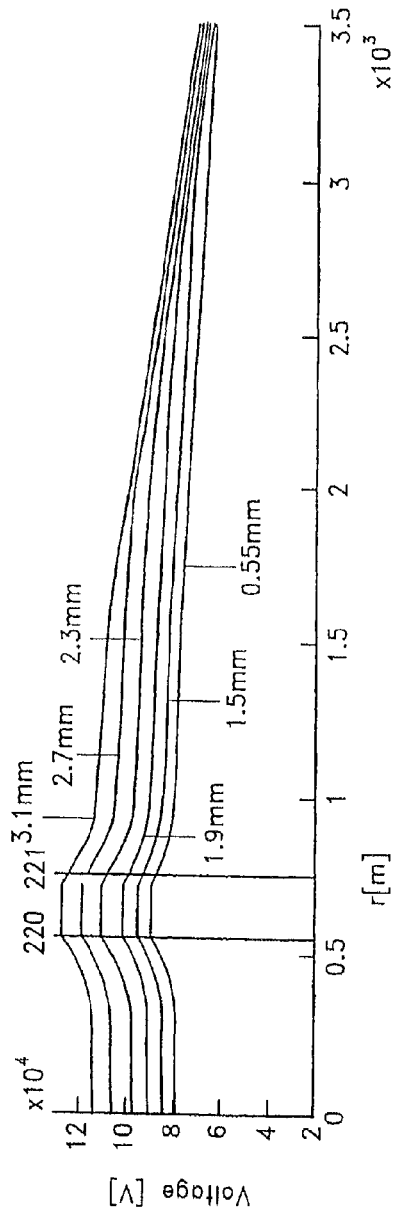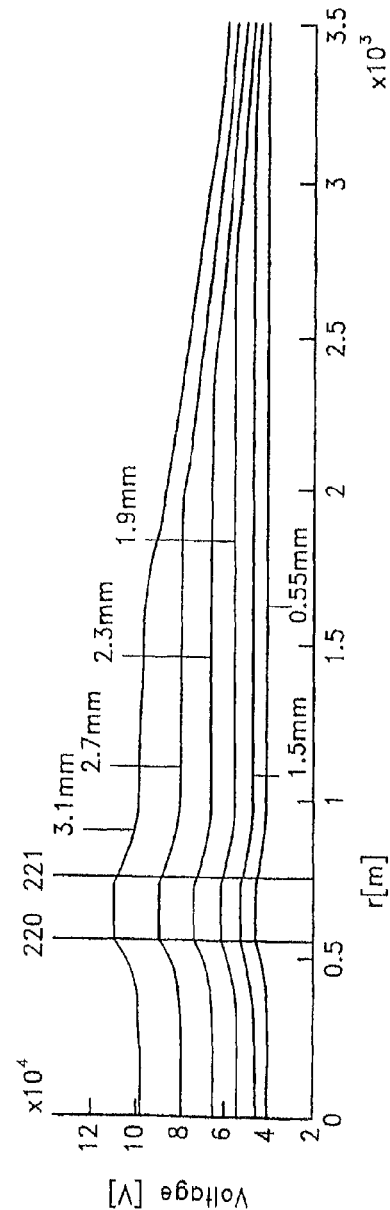
FIG. 7B
FIG. 7C

DEVICES, SYSTEMS, AND METHODS FOR REMOVING CONTRAST FROM LUMINAL ORGANS

PRIORITY

This U.S. Utility patent application is a continuation-in-part application of, and claims priority to, U.S. patent application Ser. No. 11/891,981, filed Aug. 14, 2007, now U.S. Pat. No. 8,114,143, which is related to, claims the priority benefit of, and is a divisional application of U.S. patent application Ser. No. 10/782,149, filed Feb. 19, 2004, issued as U.S. Pat. No. 7,454,244 on Nov. 18, 2008, which claims priority to U.S. Provisional Patent Application Ser. No. 60/449,266, filed Feb. 21, 2003, U.S. Provisional Patent Application Ser. No. 60/493,145, filed Aug. 7, 2003, and U.S. Provisional Patent Application Ser. No. 60/502,139, filed Sep. 11, 2003. The contents of each of these applications are hereby incorporated by reference in their entirety into this disclosure.

BACKGROUND

Coronary heart disease (CHD) is commonly caused by atherosclerotic narrowing of the coronary arteries and is likely to produce angina pectoris, heart attacks or a combination. CHD caused 466,101 deaths in the USA in 1997 and is one of the leading causes of death in America today. Approximately, 12 million people alive today have a history of heart attack, angina pectoris or both. The break down for males and females is 49% and 51%, respectively. This year, an estimated 1.1 million Americans will have a new or recurrent coronary attack, and more than 40% of the people experiencing these attacks will die as a result. About 225,000 people a year die of coronary attack without being hospitalized. These are sudden deaths caused by cardiac arrest, usually resulting from ventricular fibrillation. More than 400,000 Americans and 800,000 patients world-wide undergo a non-surgical coronary artery interventional procedure each year. Although only introduced in the 1990s, in some laboratories intra-coronary stents are used in 90% of these patients.

Stents increase minimal coronary lumen diameter to a greater degree than percutaneous transluminal coronary angioplasty (PTCA) alone according to the results of two randomized trials using the Palmaz-Schatz stent. These trials compared two initial treatment strategies: stenting alone and PTCA with "stent backup" if needed. In the STRESS trial, there was a significant difference in successful angiographic outcome in favor of stenting (96.1% vs. 89.6%).

Intravascular Ultrasound

Currently intravascular ultrasound is the method of choice to determine the true diameter of the diseased vessel in order to size the stent correctly. The term "vessel," as used herein, refers generally to any hollow, tubular, or luminal organ. The tomographic orientation of ultrasound enables visualization of the full 360° circumference of the vessel wall and permits direct measurements of lumen dimensions, including minimal and maximal diameter and cross-sectional area. Information from ultrasound is combined with that obtained by angiography. Because of the latticed characteristics of stents, radiographic contrast material can surround the stent, producing an angiographic appearance of a large lumen, even when the stent struts are not in full contact with the vessel wall. A large observational ultrasound study after angio-graphically guided stent deployment revealed an average residual plaque area of 51% in a comparison of minimal stent diameter with reference segment diameter, and incomplete wall apposition was frequently observed. In this cohort, additional balloon inflations resulted in a final average residual plaque area of 34%, even though the final angiographic percent stenosis was negative (20.7%). These investigators used ultrasound to guide deployment.

However, using intravascular ultrasound as mentioned above requires a first step of advancement of an ultrasound catheter and then withdrawal of the ultrasound catheter before coronary angioplasty thereby adding additional time to the stent procedure. Furthermore, it requires an ultrasound machine. This adds significant cost and time and more risk to the procedure.

Aortic Stenosis

Aortic Stenosis (AS) is one of the major reasons for valve replacements in adult. AS occurs when the aortic valve orifice narrows secondary to valve degeneration. The aortic valve area is reduced to one fourth of its normal size before it shows a hemodynamic effect. Because the area of the normal adult valve orifice is typically 3.0 to 4.0 $cm^2$, an area 0.75-1.0 $cm^2$ is usually not considered severe AS. When stenosis is severe and cardiac output is normal, the mean trans-valvular pressure gradient is generally >50 mmHg. Some patients with severe AS remain asymptomatic, whereas others with only moderate stenosis develop symptoms. Therapeutic decisions, particularly those related to corrective surgery, are based largely on the presence or absence of symptoms.

The natural history of AS in the adult consists of a prolonged latent period in which morbidity and mortality are very low. The rate of progression of the stenotic lesion has been estimated in a variety of hemodynamic studies performed largely in patients with moderate AS. Cardiac catheterization and Doppler echocardiographic studies indicate that some patients exhibit a decrease in valve area of 0.1-0.3 $cm^2$ per year; the average rate of change is 0.12 $cm^2$ per year. The systolic pressure gradient across the valve may increase by as much as 10 to 15 mmHg per year. However, more than half of the reported patients showed little or no progression over a 3-9 year period. Although it appears that progression of AS can be more rapid in patients with degenerative calorific disease than in those with congenital or rheumatic disease, it is not possible to predict the rate of progression in an individual patient.

Eventually, symptoms of angina, syncope, or heart failure develop after a long latent period, and the outlook changes dramatically. After onset of symptoms, average survival is <2-3 years. Thus, the development of symptoms identifies a critical point in the natural history of AS.

Many asymptomatic patients with severe AS develop symptoms within a few years and require surgery. The incidence of angina, dyspnea, or syncope in asymptomatic patients with Doppler outflow velocities of 4 m/s has been reported to be as high as 38% after 2 years and 79% after 3 years. Therefore, patients with severe AS require careful monitoring for development of symptoms and progressive disease.

Indications for Cardiac Catheterization

In patients with AS, the indications for cardiac catheterization and angiography are to assess the coronary circulation (to confirm the absence of coronary artery disease) and to confirm or clarify the clinical diagnosis of AS severity. If echocardiographic data are typical of severe isolated. AS, coronary angiography may be all that is needed before aortic valve replacement (AVR). Complete left- and right-heart catheterization may be necessary to assess the hemodynamic severity of AS if there is a discrepancy between clinical and echocardiographic data or evidence of associated valvular or congenital disease or pulmonary hypertension.

The pressure gradient across a stenotic valve is related to the valve orifice area and transvalvular flow through Bernoulli's principle. Thus, in the presence of depressed cardiac output, relatively low pressure gradients are frequently obtained in patients with severe AS. On the other hand, during exercise or other high-flow states, systolic gradients can be measured in minimally stenotic valves. For these reasons, complete assessment of AS requires (1) measurement of transvalvular flow, (2) determination of the transvalvular pressure gradient, and (3) calculation of the effective valve area. Careful attention to detail with accurate measurements of pressure and flow is important, especially in patients with low cardiac output or a low transvalvular pressure gradient.

Problems with Current Aortic Valve Area Measurements

Patients with severe AS and low cardiac output are often present with only modest transvalvular pressure gradients (i.e., <30 mmHg). Such patients can be difficult to distinguish from those with low cardiac output and only mild to moderate AS. In both situations, the low-flow state and low pressure gradient contribute to a calculated effective valve area that can meet criteria for severe AS. The standard valve area formula (simplified Hakki formula which is valve area=cardiac output/[pressure gradient]$^{1/2}$) is less accurate and is known to underestimate the valve area in low-flow states; under such conditions, it should be interpreted with caution. Although valve resistance is less sensitive to flow than valve area, resistance calculations have not been proved to be substantially better than valve area calculations.

In patients with low gradient stenosis and what appears to be moderate to severe AS, it may be useful to determine the transvalvular pressure gradient and calculate valve area and resistance during a baseline state and again during exercise or pharmacological (i.e., dobutamine infusion) stress. Patients who do not have true, anatomically severe stenosis exhibit an increase in the valve area during an increase in cardiac output. In patients with severe AS, these changes may result in a calculated valve area that is higher than the baseline calculation but that remains in the severe range, whereas in patients without severe AS, the calculated valve area will fall outside the severe range with administration of dobutamine and indicate that severe AS is not present.

There are many other limitations in estimating aortic valve area in patients with aortic stenosis using echocardiography and cardiac catheterization. Accurate measurement of the aortic valve area in patients with aortic stenosis can be difficult in the setting of low cardiac output or concomitant aortic or mitral regurgitations. Concomitant aortic regurgitation or low cardiac output can overestimate the severity of aortic stenosis. Furthermore, because of the dependence of aortic valve area calculation on cardiac output, any under or overestimation of cardiac output will cause inaccurate measurement of valve area. This is particularly important in patients with tricuspid regurgitation. Falsely measured aortic valve area could cause inappropriate aortic valve surgery in patients who do not need it.

Other Visceral Organs

Visceral organs such as the gastrointestinal tract and the urinary tract serve to transport luminal contents (fluids) from one end of the organ to the other end or to an absorption site. The esophagus, for example, transports swallowed material from the pharynx to the stomach. Diseases may affect the transport function of the organs by changing the luminal cross-sectional area, the peristalsis generated by muscle, or by changing the tissue components. For example, strictures in the esophagus and urethra constitute a narrowing of the organ where fibrosis of the wall may occur. Strictures and narrowing can be treated with distension, much like the treatment of plaques in the coronary arteries.

Contrast Agents

A growing number of cardiac catheterization procedures, as well as the complexity of the lesions, has led to increased administration of radiographic contrast agents. A serious complication of exposure to iodinated contrast media, for example, is contrast-induced nephropathy (CIN) which can cause renal dysfunction. CIN is associated with increased in hospital mortality, poor long-term survival rates, and cost. The approach of removal of contrast media from the coronary sinus before it circulates throughout the body and to the kidney has been suggested. However, previous attempts to remove contrast from the coronary sinus, however, have not been automatic and have lacked a sensitive, simple and inexpensive sensor which minimizes the amount of blood removed.

The CIN Task Force recommends limiting the volume of contrast during angiography and percutaneous coronary intervention in high-risk patients to <30 ml and <100 ml, respectively. These recommendations provide support to the notion that pre-renal removal of contrast may reduce the risk of developing CIN in patients undergoing contrast exposure.

Thus, a need exists in the art for devices, systems, and methods for removing contrast from luminal organs. Such a system should be sensitive, relative inexpensive, easy to operate, and effective while minimizing overall blood loss during the removal process.

BRIEF SUMMARY

In at least one embodiment of a device for removing contrast from a luminal organ of the present disclosure, the device comprises an elongated body having at least one lumen extending therethrough and an aperture defined along the elongated body, said aperture configured to facilitate withdrawal of contrast from a mammalian luminal organ, a first detector for detecting a contrast present within the mammalian luminal organ, the detector positioned at or near a distal end of the elongated body, an inflatable balloon coupled to the elongated body proximal to the detector, and a second detector for detecting balloon inflation, the second detector positioned along the elongated body within the balloon. In another embodiment, and when the first detector detects the contrast present within the mammalian luminal organ, the device is operable to withdraw contrast from the mammalian luminal organ through the aperture of the elongated body. In at least one embodiment, the first detector comprises a first pair of excitation electrodes located on the elongated body, and a first pair of detection electrodes located on the elongated body in between the first pair of excitation electrodes, wherein the first detector is capable of obtaining a conductance measurement of a fluid within the mammalian luminal organ. In an additional embodiment, the second detector comprises a second pair of excitation electrodes located on the elongated body, and a second pair of detection electrodes located on the elongated body in between the second pair of excitation electrodes, wherein the second detector is capable of obtaining a conductance measurement of a fluid within the balloon to determine balloon cross-sectional area. In another embodiment, at least one excitation electrode of the first pair of excitation electrodes and at least one excitation electrode of the second pair of excitation electrodes is/are in communication with a current source capable of supplying electrical current to said electrodes.

In at least one embodiment of a device for removing contrast from a luminal organ of the present disclosure, the aperture is defined along the elongated body proximal to the first detector. In an additional embodiment, the device further comprises a data acquisition and processing system capable of receiving conductance data from the detector. In another embodiment, the device is capable of removing contrast from the mammalian luminal organ by introducing suction at or a near a proximal end of the device to facilitate contrast entry into the lumen of the elongated body through the aperture.

In at least one embodiment of a device for removing contrast from a luminal organ of the present disclosure, the device further comprises a suction apparatus coupled to the elongated body, and an electronic module coupled to the suction apparatus and the first detector, wherein when the first detector detects contrast within the mammalian luminal organ, the electronic module activates the suction apparatus to withdraw contrast from the mammalian luminal organ. In another embodiment, the device further comprises an inflation source coupled to the balloon, and an electronic module coupled to the inflation source and the first detector, wherein when the first detector detects contrast within the mammalian luminal organ, the electronic module activates the inflation source to inflate the inflatable balloon. In yet another embodiment, and when a fluid is injected through the lumen of the elongated body into the balloon, the second detector is capable of obtaining a fluid conductance measurement within the balloon, wherein the fluid conductance measurement is useful to determine balloon cross-sectional area.

In at least one embodiment of a method for removing contrast from a luminal organ of the present disclosure, the method comprises the steps of inserting at least part of a device for removing contrast into a mammalian luminal organ, the device having a first detector and a balloon positioned along an elongated body, at least one lumen extending therethrough, and an aperture defined along the elongated body, detecting contrast present within the mammalian luminal organ, inflating the balloon to prohibit fluid flow within the mammalian luminal organ proximal to the balloon, removing contrast through the aperture of the device, and ceasing removal of contrast from the mammalian luminal organ when a threshold amount of contrast is no longer detected within the mammalian luminal organ. In another embodiment, the step of detecting contrast is performed using the first detector of the device. In yet another embodiment, the step of inflating the balloon is performed using an inflation source upon detection of contrast present within the mammalian luminal organ. In various embodiments, the steps of inflating the balloon and removing contrast are performed simultaneously.

In at least one embodiment of a method for removing contrast from a luminal organ of the present disclosure, the step of inflating the balloon is performed by inflating the balloon to a desired size. In another embodiment, the desired size corresponds to a size detected by a second detector positioned along the elongated body within the balloon. In an additional embodiment, the desired size corresponds to a size so that contrast is prevented from escaping past the balloon but does not cause injury to the mammalian luminal organ. In another embodiment, the step of detecting contrast comprises the steps of obtaining one or more initial conductance measurements within the mammalian luminal organ using the first detector, the one or more initial conductance measurements obtained without contrast present therein, and obtaining one or more subsequent conductance measurements within the mammalian luminal organ using the first detector, wherein at least one of the one or more subsequent conductance measurements is a threshold percentage lower than at least one of the one or more initial conductance measurements. In yet another embodiment, the threshold percentage is at least approximately 10% lower than at least one of the one or more initial conductance measurements.

In at least one embodiment of a method for removing contrast from a luminal organ of the present disclosure, the method further comprises the step of deflating the balloon to permit fluid flow within the mammalian luminal organ proximal to the balloon. In another embodiment, the deflation step is performed in response to at least a partial conductance measurement recovery. In yet another embodiment, the partial conductance measurement recovery is approximately within 5% of at least one of the one or more initial conductance measurements.

In at least one embodiment of a method for removing contrast from a luminal organ of the present disclosure, the method is performed to reduce or eliminate a risk of contrast-induced nephropathy. In another embodiment, the mammalian luminal organ comprises a heart, and wherein the device is inserted within a coronary sinus of the heart. In yet another embodiment, the step of removing contrast removes no more than approximately 100 ml of contrast.

In at least one embodiment of a system for removing contrast from a luminal organ of the present disclosure, the system comprises an elongated body having at least one lumen extending therethrough and an aperture defined along the elongated body, said aperture configured to facilitate withdrawal of contrast from a mammalian luminal organ, a suction apparatus in fluid communication with and coupled to the elongated body, a first detector for detecting a contrast present within a mammalian luminal organ, the detector positioned at or near a distal end of the elongated body, an inflatable balloon coupled to the elongated body proximal to the detector, an inflation source in fluid communication with and coupled to the balloon, a second detector for detecting balloon inflation, the second detector positioned along the elongated body within the balloon, at least one current source coupled to the first detector and the second detector, and an electronic module coupled to the suction apparatus, the inflation source, and the first detector, the electronic module operable to activate the suction apparatus and the inflation source upon detection of contrast by the first detector.

BRIEF DESCRIPTION OF THE DRAWINGS

FIG. 1A shows a balloon catheter having impedance measuring electrodes supported in front of the stenting balloon, according to an embodiment of the present disclosure;

FIG. 1B shows a balloon catheter having impedance measuring electrodes within and in front of the balloon, according to an embodiment of the present disclosure;

FIG. 1C shows a catheter having an ultrasound transducer within and in front of balloon, according to an embodiment of the present disclosure;

FIG. 1D shows a catheter without a stenting balloon, according to an embodiment of the present disclosure;

FIG. 1E shows a guide catheter with wire and impedance electrodes, according to an embodiment of the present disclosure;

FIG. 1F shows a catheter with multiple detection electrodes, according to an embodiment of the present disclosure;

FIG. 7B shows the voltage recorded by a conductance catheter with a radius of 0.55 mm for various size vessels (vessel radii of 3.1, 2.7, 2.3, 1.9, 1.5 and 0.55 mm for the six curves, respectively) when a 0.5% NaCl bolus is injected into the treatment site, according to an embodiment of the present disclosure;

FIG. 7C shows the voltage recorded by a conductance catheter with a radius of 0.55 mm for various size vessels (vessel radii of 3.1, 2.7, 23, 1.9, 1.5 and 0.55 mm for the six curves, respectively) when a 1.5% NaCl bolus is injected into the treatment site, according to an embodiment of the present disclosure;

DETAILED DESCRIPTION

Figure 2B:
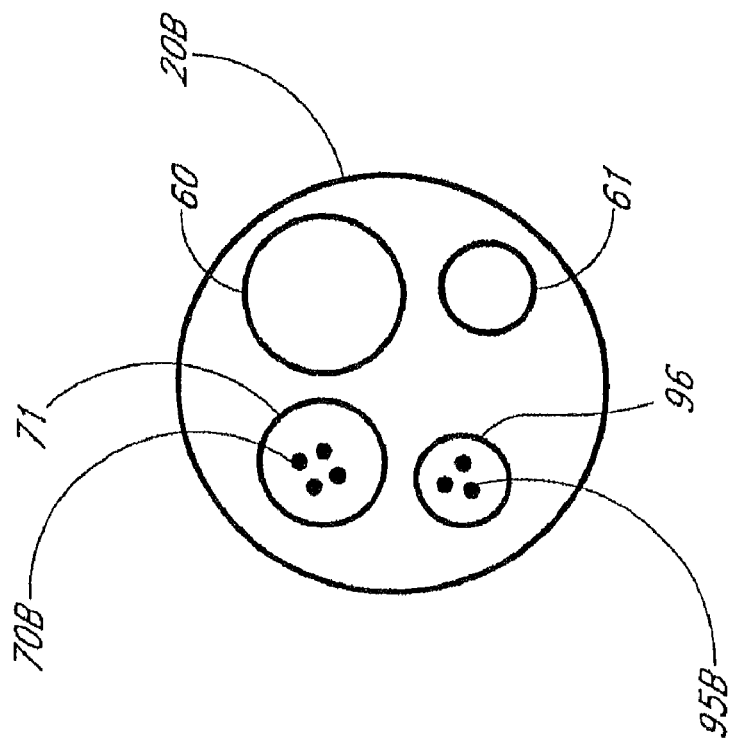
FIG. 2B shows a catheter in cross-section proximal to the location of the sensors showing the leads run in separate lumens, according to an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

This present disclosure makes accurate measures of the luminal cross-sectional area of organ stenosis within acceptable limits to enable accurate and scientific stent sizing and placement in order to improve clinical outcomes by avoiding under or over deployment and under or over sizing of a stent which can cause acute closure or in-stent re-stenosis. In one embodiment, an angioplasty or stent balloon includes impedance electrodes supported by the catheter in front of the balloon. These electrodes enable the immediate measurement of the cross-sectional area of the vessel during the balloon advancement. This provides a direct measurement of non-stenosed area and allows the selection of the appropriate stent size. In one approach, error due to the loss of current in the wall of the organ and surrounding tissue is corrected by injection of two solutions of NaCl or other solutions with known conductivities. In another embodiment impedance electrodes are located in the center of the balloon in order to deploy the stent to the desired cross-sectional area. These embodiments and procedures substantially improve the accuracy of stenting and the outcome and reduce the cost.

Other embodiments make diagnosis of valve stenosis more accurate and more scientific by providing a direct accurate measurement of cross-sectional area of the valve annulus, independent of the flow conditions through the valve. Other embodiments improve evaluation of cross-sectional area and flow in organs like the gastrointestinal tract and the urinary tract.

Embodiments of the present disclosure overcome the problems associated with determination of the size (cross-sectional area) of luminal organs, such as, for example, in the coronary arteries, carotid, femoral, renal and iliac arteries, aorta, gastrointestinal tract, urethra and ureter. Embodiments also provide methods for registration of acute changes in wall conductance, such as, for example, due to edema or acute damage to the tissue, and for detection of muscle spasms/contractions.

As described below, in one preferred embodiment, there is provided an angioplasty catheter with impedance electrodes near the distal end 19 of the catheter (i.e., in front of the balloon) for immediate measurement of the cross-sectional area of a vessel lumen during balloon advancement. This catheter includes electrodes for accurate detection of organ luminal cross-sectional area and ports for pressure gradient measurements. Hence, it is not necessary to change catheters such as with the current use of intravascular ultrasound. In one preferred embodiment, the catheter provides direct measurement of the non-stenosed area, thereby allowing the selection of an appropriately sized stent. In another embodiment, additional impedance electrodes may be incorporated in the center of the balloon on the catheter in order to deploy the stent to the desired cross-sectional area. The procedures described herein substantially improve the accuracy of stenting and improve the cost and outcome as well.

In another embodiment, the impedance electrodes are embedded within a catheter to measure the valve area directly and independent of cardiac output or pressure drop and therefore minimize errors in the measurement of valve area. Hence, measurements of area are direct and not based on calculations with underlying assumptions. In another embodiment, pressure sensors can be mounted proximal and distal to the impedance electrodes to provide simultaneous pressure gradient recording.

Catheter

We designed and build the impedance or conductance catheters illustrated in FIGS. 1A-1F. With reference to the exemplary embodiment shown in FIG. 1A, four wires were threaded through one of the 2 lumens of a 4 Fr catheter. Here, electrodes 26 and 28, are spaced 1 mm apart and form the inner (detection) electrodes. Electrodes 25 and 27 are spaced 4-5 mm from either side of the inner electrodes and form the outer (excitation) electrodes.

In one approach, dimensions of a catheter to be used for any given application depend on the optimization of the potential field using finite element analysis described below. For small organs or in pediatric patients the diameter of the catheter may be as small as 0.3 mm. In large organs the diameter may be significantly larger depending on the results of the optimization based on finite element analysis. The balloon size will typically be sized according to the preferred dimension of the organ after the distension. The balloon may be made of materials, such as, for example, polyethylene, latex, polyestherurethane, or combinations thereof. The thickness of the balloon will typically be on the order of a few microns. The catheter will typically be made of PVC or polyethylene, though other materials may equally well be used. The excitation and detection electrodes typically surround the catheter as ring electrodes but they may also be point electrodes or have other suitable configurations. These electrodes may be made of any conductive material, preferably of platinum iridium or a carbon-coasted surface to avoid fibrin deposits. In the preferred embodiment, the detection electrodes are spaced with 0.5-1 mm between them and with a distance between 4-7 mm to the excitation electrodes on small catheters. The dimensions of the catheter selected for a treatment depend on the size of the vessel and are preferably determined in part on the results of finite element analysis, described below. On large catheters, for use in larger vessels and other visceral hollow organs, the electrode distances may be larger.

Referring to FIGS. 1A, 1B, 1C and 1D, several embodiments of the catheters are illustrated. The catheters shown contain to a varying degree different electrodes, number and optional balloon(s). With reference to the embodiment shown in FIG. 1A, there is shown an impedance catheter 20 with 4 electrodes 25, 26, 27 and 28 placed close to the tip 19 of the catheter. Proximal to these electrodes is an angiography or stenting balloon 30 capable of being used for treating stenosis. Electrodes 25 and 27 are excitation electrodes, while electrodes 26 and 28 are detection electrodes, which allow measurement of cross-sectional area during advancement of the catheter, as described in further detail below. The portion of the catheter 20 within balloon 30 includes an infusion port 35 and a pressure port 36.

The catheter 20 may also advantageously include several miniature pressure transducers (not shown) carried by the catheter or pressure ports for determining the pressure gradient proximal at the site where the cross-sectional area is measured. The pressure is preferably measured inside the balloon and proximal, distal to and at the location of the cross-sectional area measurement, and locations proximal and distal thereto, thereby enabling the measurement of pressure recordings at the site of stenosis and also the measurement of pressure-difference along or near the stenosis. In one embodiment, shown in FIG. 1A, Catheter 20 advantageously includes pressure port 90 and pressure port 91 proximal to or at the site of the cross-sectional measurement for evaluation of pressure gradients. As described below with reference to FIGS. 2A, 2B and 3, in one embodiment, the pressure ports are connected by respective conduits in the catheter 20 to pressure sensors in the data acquisition system 100. Such pressure sensors are well known in the art and include, for example, fiber-optic systems, miniature strain gauges, and perfused low-compliance manometry.

In one embodiment, a fluid-filled silastic pressure-monitoring catheter is connected to a pressure transducer. Luminal pressure can be monitored by a low compliance external pressure transducer coupled to the infusion channel of the catheter. Pressure transducer calibration was carried out by applying 0 and 100 mmHg of pressure by means of a hydrostatic column.

In one embodiment, shown in FIG. 1B, the catheter 39 includes another set of excitation electrodes 40, 41 and detection electrodes 42, 43 located inside the angioplastic or stenting balloon 30 for accurate determination of the balloon cross-sectional area during angioplasty or stent deployment. These electrodes are in addition to electrodes 25, 26, 27 and 28.

In one embodiment, the cross-sectional area may be measured using a two-electrode system. In another embodiment, illustrated in FIG. 1F, several cross-sectional areas can be measured using an array of 5 or more electrodes. Here, the excitation electrodes 51, 52, are used to generate the current while detection electrodes 53, 54, 55, 56 and 57 are used to detect the current at their respective sites.

The tip of the catheter can be straight, curved or with an angle to facilitate insertion into the coronary arteries or other lumens, such as, for example, the biliary tract. The distance between the balloon and the electrodes is usually small, in the 0.5-2 cm range but can be closer or further away, depending on the particular application or treatment involved.

In another embodiment, shown in FIG. 1C the catheter 21 has one or more imaging or recording device, such as, for example, ultrasound transducers 50 for cross-sectional area and wall thickness measurements. As shown in this embodiment, the transducers 50 are located near the distal tip 19 of the catheter 21.

FIG. 1D shows an embodiment of the impedance catheter 22 without an angioplastic or stenting balloon. This catheter also possesses an infusion or injection port 35 located proximal relative to the excitation electrode 25 and pressure port 36.

With reference to the embodiment shown in FIG. 1E, the electrodes 25, 26, 27, 28 can also be built onto a wire 18, such as, for example, a pressure wire, and inserted through a guide catheter 23 where the infusion of bolus can be made through the lumen of the guide catheter 37.

With reference to the embodiments shown in FIGS. 1A, 1B, 1C, 1D, 1E and 1F, the impedance catheter advantageously includes optional ports 35, 36, 37 for suction of contents of the organ or infusion of fluid. The suction/infusion port 35, 36, 37 can be placed as shown with the balloon or elsewhere both proximal or distal to the balloon on the catheter. The fluid inside the balloon can be any biologically compatible conducting fluid. The fluid to inject through the infusion port or ports can be any biologically compatible fluid but the conductivity of the fluid is selected to be different from that of blood (e.g., NaCl).

In another embodiment (not illustrated), the catheter contains an extra channel for insertion of a guide wire to stiffen the flexible catheter during the insertion or data recording. In yet another embodiment (not illustrated), the catheter includes a sensor for measurement of the flow of fluid in the body organ.

System for Determining Cross-Sectional Area and Pressure Gradient

The operation of the impedance catheter 20 is as follows: With reference to the embodiment shown in FIG. 1A for electrodes 25, 26, 27, 28, conductance of current flow through the organ lumen and organ wall and surrounding tissue is parallel; i.e., $$G(z, t) = \frac{CSA(z, t) \cdot C_b}{L} + G_p(z, t) \quad [1a]$$

where $G_p(z,t)$ is the effective conductance of the structure outside the bodily fluid (organ wall and surrounding tissue), and $C_b$ is the specific electrical conductivity of the bodily fluid which for blood generally depends on the temperature, hematocrit and orientation and deformation of blood cells and L is the distance between the detection electrodes. Equation [1] can be rearranged to solve for cross sectional area CSA(t), with a correction factor, $\alpha$, if the electric field is non-homogeneous, as $$CSA(z, t) = \frac{L}{\alpha C_b} [G(z, t) = G_p(z, t)] \quad [1b]$$

where $\alpha$ would be equal to 1 if the field were completely homogeneous. The parallel conductance, $G_p$, is an offset error that results from current leakage. $G_p$ would equal 0 if all of the current were confined to the blood and hence would correspond to the cylindrical model given by Equation [10]. In one approach, finite element analysis is used to properly design the spacing between detection and excitation electrodes relative to the dimensions of the vessel to provide a nearly homogenous field such that a can be considered equal to 1. Our simulations show that a homogenous or substantially homogenous field is provided by (1) the placement of detection electrodes substantially equidistant from the excitation electrodes and (2) maintaining the distance between the detection and excitation electrodes substantially comparable to the vessel diameter. In one approach, a homogeneous field is achieved by taking steps (1) and/or (2) described above so that $\alpha$ is equals 1 in the foregoing analysis.

At any given position, z, along the long axis of organ and at any given time, t, in the cardiac cycle, $G_p$ is a constant. Hence, two injections of different concentrations and/or conductivities of NaCl solution give rise to two Equations:

$$C_1 \cdot CSA(z,t) + L \cdot G_p(z,t) = L \cdot G_1(z,t) \quad [2]$$

and $$C_2 \cdot CSA(z,t) + L \cdot G_p(z,t) = L \cdot G_2(z,t) \quad [3]$$

which can be solved simultaneously for CSA and $G_p$ as $$CSA(z, t) = L \frac{[G_2(z, t) - G_1(z, t)]}{[C_2 - C_1]} \quad [4]$$

and $$G_p(z, t) = \frac{[C_2 \cdot G_1(z, t) - C_1 \cdot G_2(z, t)]}{[C_2 - C_1]} \quad [5]$$

where subscript "1" and subscript "2" designate any two injections of different NaCl concentrations and/or conductivities. For each injection k, $C_k$ gives rise to $G_k$ which is measured as the ratio of the root mean square of the current divided by the root mean square of the voltage. The $C_k$ is typically determined through in vitro calibration for the various NaCl concentrations and/or conductivities. The concentration of NaCl used is typically on the order of 0.45 to 1.8%. The volume of NaCl solution is typically about 5 ml, but sufficient to displace the entire local vascular blood volume momentarily. The values of CSA(t) and $G_p$(t) can be determined at end-diastole or end-systole (i.e., the minimum and maximum values) or the mean thereof.

Once the CSA and $G_p$ of the vessel are determined according to the above embodiment, rearrangement of Equation [1] allows the calculation of the specific electrical conductivity of blood in the presence of blood flow as $$C_b = \frac{L}{CSA(z, t)} [G(z, t) - G_p(z, t)] \quad [6]$$

In this way, Equation [1b] can be used to calculate the CSA continuously (temporal variation as for example through the cardiac cycle) in the presence of blood.

In one approach, a pull or push through is used to reconstruct the vessel along its length. During a long injection (e.g., 10-15 s), the catheter can be pulled back or pushed forward at constant velocity U. Equation [1b] can be expressed as $$CSA(U \cdot t, t) = \frac{L}{C_b} [G(U \cdot t, t) - G_p(U \cdot (t, t))] \quad [7]$$

where the axial position, z, is the product of catheter velocity, U, and time, t; i.e., z=U·t, For the two injections, denoted by subscript "1" and subscript "2", respectively, we can consider different time points T1, T2, etc. such that Equation [7] can be written as $$CSA_1(U \cdot T_1, t) = \frac{L}{C_1} [G_1(U \cdot T_1, t) - G_{p1}(U \cdot T_1, t)] \quad [8a]$$

$$CSA_1(U \cdot T_1, t) = \frac{L}{C_2} [G_2(U \cdot T_1, t) - G_{p1}(U \cdot T_1, t)] \quad [8b]$$

and $$CSA_2(U \cdot T_2, t) = \frac{L}{C_1} [G_1(U \cdot T_2, t) - G_{p2}(U \cdot T_2, t)] \quad [9a]$$

$$CSA_2(U \cdot T_2, t) = \frac{L}{C_2} [G_2(U \cdot T_2, t) - G_{p2}(U \cdot T_2, t)] \quad [9b]$$

and so on. Each set of Equations [8a], [8b] and [9a], [9b], etc. can be solved for $CSA_1$, $G_{p1}$ and $CSA_2$, $G_{p2}$, respectively. Hence, we can measure the CSA at various time intervals and hence of different positions along the vessel to reconstruct the length of the vessel. In one embodiment, the data on the CSA and parallel conductance as a function of longitudinal position along the vessel can be exported from an electronic spreadsheet, such as, for example, an Excel file, to AutoCAD where the software uses the coordinates to render a 3-Dimensional vessel on the monitor.

For example, in one exemplary approach, the pull back reconstruction was made during a long injection where the catheter was pulled back at constant rate by hand. The catheter was marked along its length such that the pull back was made at 2 mm/sec. Hence, during a 10 second injection, the catheter was pulled back about 2 cm. The data was continuously measured and analyzed at every two second interval; i.e., at every 4 mm. Hence, six different measurements of CSA and $G_p$ were made which were used to reconstruction the CSA and $G_p$ along the length of the 2 cm segment.

Operation of the impedance catheter 39: With reference to the embodiment shown in FIG. 1B, the voltage difference between the detection electrodes 42 and 43 depends on the magnitude of the current (I) multiplied by the distance (D) between the detection electrodes and divided by the conductivity (C) of the fluid and the cross-sectional area (CSA) of the artery or other organs into which the catheter is introduced. Since the current (I), the distance (L) and the conductivity (C) normally can be regarded as calibration constants, an inverse relationship exists between the voltage difference and the CSA as shown by the following Equations:

$$\Delta V = \frac{I \cdot L}{C \cdot CSA} \quad [10a]$$

or $$CSA = \frac{G \cdot L}{C} \quad [10b]$$

where G is conductance expressed as the ratio of current to voltage (I/ΔV). Equation [10] is identical to Equation [1b] if we neglect the parallel conductance through the vessel wall and surrounding tissue because the balloon material acts as an insulator. This is the cylindrical model on which the conductance method is used.

As described below with reference to FIGS. 2A, 2B, 3, 4 and 5, the excitation and detection electrodes are electrically connected to electrically conductive leads in the catheter for connecting the electrodes to the data acquisition system 100.

Figure 2A:
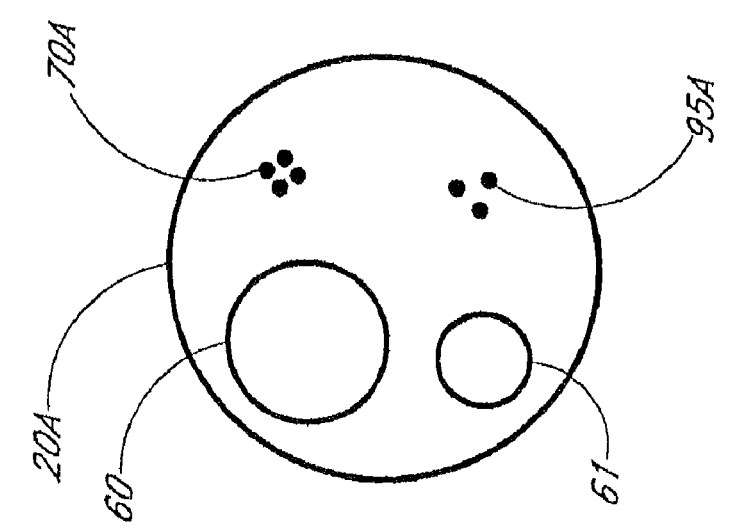
FIG. 2A shows a catheter in cross-section proximal to the location of the sensors showing the leads embedded in the material of the probe, according to an embodiment of the present disclosure.

FIGS. 2A and 2B illustrate two embodiments 20A and 20B of the catheter in cross-section. Each embodiment has a lumen 60 for inflating and deflating the balloon and a lumen 61 for suction and infusion. The sizes of these lumens can vary in size. The impedance electrode electrical leads 70A are embedded in the material of the catheter in the embodiment in FIG. 2A, whereas the electrode electrical leads 70B are tunneled through a lumen 71 formed within the body of catheter 70B in FIG. 2B.

Pressure conduits for perfusion manometry connect the pressure ports 90, 91 to transducers included in the data acquisition system 100. As shown in FIG. 2A pressure conduits 95A may be formed in 20A. In another embodiment, shown in FIG. 2B, pressure conduits 95B constitute individual conduits within a tunnel 96 formed in catheter 20B. In the embodiment described above where miniature pressure transducers are carried by the catheter, electrical conductors will be substituted for these pressure conduits.

Figure 3:
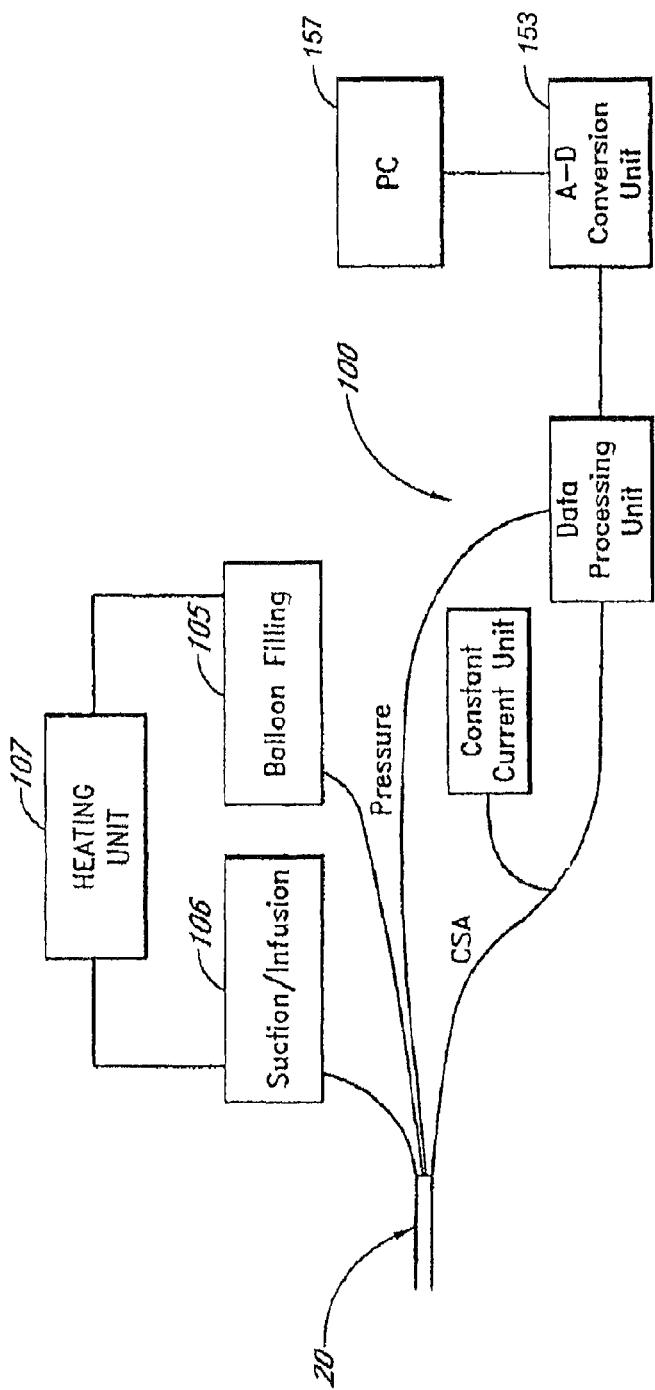
FIG. 3 is a schematic of one embodiment of the system showing a catheter carrying impedance measuring electrodes connected to the data acquisition equipment and excitation unit for the cross-sectional area measurement, according to an embodiment of the present disclosure.

With reference to FIG. 3, in one embodiment, the catheter 20 connects to a data acquisition system 100, to a manual or automatic system 105 for distension of the balloon and to a system 106 for infusion of fluid or suction of blood. The fluid will be heated to 37-39° or equivalent to body temperature with heating unit 107. The impedance planimetry system typically includes a constant current unit, amplifiers and signal conditioners. The pressure system typically includes amplifiers and signal conditioners. The system can optionally contain signal conditioning equipment for recording of fluid flow in the organ.

In one preferred embodiment, the system is pre-calibrated and the probe is available in a package. Here, the package also preferably contains sterile syringes with the fluids to be injected. The syringes are attached to the machine and after heating of the fluid by the machine and placement of the probe in the organ of interest, the user presses a button that initiates the injection with subsequent computation of the desired parameters. The CSA and parallel conductance and other relevant measures such as dispensability, tension, etc. will typically appear on the display panel in the PC module 160. Here, the user can then remove the stenosis by distension or by placement of a stent.

If more than one CSA is measured, the system can contain a multiplexer unit or a switch between CSA channels. In one embodiment, each CSA measurement will be through separate amplifier units. The same may account for the pressure channels.

In one embodiment, the impedance and pressure data are analog signals which are converted by analog-to-digital converters 150 and transmitted to a computer 160 for on-line display, on-line analysis and storage. In another embodiment, all data handling is done on an entirely analog basis. The analysis advantageously includes software programs for reducing the error due to conductance of current in the organ wall and surrounding tissue and for displaying the 2D or 3D-geometry of the CSA distribution along the length of the vessel along with the pressure gradient. In one embodiment of the software, a finite element approach or a finite difference approach is used to derive the CSA of the organ stenosis taking parameters such as conductivities of the fluid in the organ and of the organ wall and surrounding tissue into consideration. In another embodiment, simpler circuits are used; e.g., based on making two or more injections of different NaCl solutions to vary the resistivity of fluid in the vessel and solving the two simultaneous Equations [2] and [3] for the CSA and parallel conductance (Equations [4] and [5], respectively). In another embodiment, the software contains the code for reducing the error in luminal CSA measurement by analyzing signals during interventions such as infusion of a fluid into the organ or by changing the amplitude or frequency of the current from the constant current amplifier. The software chosen for a particular application, preferably allows computation of the CSA with only a small error instantly or within acceptable time during the medical procedure.

In one approach, the wall thickness is determined from the parallel conductance for those organs that are surrounded by air or non-conducting tissue. In such cases, the parallel conductance is equal to $$G_p = \frac{CSA_w \cdot C_w}{L} \quad [11a]$$

where $CSA_W$ is the wall area of the organ and $C_W$ is the electrical conductivity through the wall. This Equation can be solved for the wall $CSA_W$ as $$CSA_w = \frac{G_p \cdot L}{C_w} \quad [11b]$$

For a cylindrical organ, the wall thickness, h, can be expressed as $$h = \frac{CSA_w}{\pi D} \quad [12]$$

where D is the diameter of the vessel which can be determined from the circular CSA (D=[4 CSA/π]$^{1/2}$).

When the CSA, pressure, wall thickness, and flow data are determined according to the embodiments outlined above, it is possible to compute the compliance (e.g., ΔCSA/ΔP), tension (e.g., P·r, where P and r are the intraluminal pressure and radius of a cylindrical organ), stress (e.g., P·r/h where h is the wall thickness of the cylindrical organ), strain (e.g., $(C-C_d)/C_d$ where C is the inner circumference and $C_d$ is the circumference in diastole) and wall shear stress (e.g., $4 \mu Q/r^3$ where $\mu$, Q and r are the fluid viscosity, flow rate and radius of the cylindrical organ for a fully developed flow). These quantities can be used in assessing the mechanical characteristics of the system in health and disease.

Method

In one approach, luminal cross-sectional area is measured by introducing a catheter from an exteriorly accessible opening (e.g., mouth, nose or anus for GI applications; or e.g., mouth or nose for airway applications) into the hollow system or targeted luminal organ. For cardiovascular applications, the catheter can be inserted into the organs in various ways; e.g., similar to conventional angioplasty. In one embodiment, an 18 gauge needle is inserted into the femoral artery followed by an introducer. A guide wire is then inserted into the introducer and advanced into the lumen of the femoral artery. A 4 or 5 Fr conductance catheter is then inserted into the femoral artery via wire and the wire is subsequently retracted. The catheter tip containing the conductance electrodes can then be advanced to the region of interest by use of x-ray (i.e., fluoroscopy). In another approach, this methodology is used on small to medium size vessels (e.g., femoral, coronary, carotid, iliac arteries, etc.).

In one approach, a minimum of two injections (with different concentrations and/or conductivities of NaCl) are required to solve for the two unknowns, CSA and $G_p$. In another approach, three injections will yield three set of values for CSA and $G_p$ (although not necessarily linearly independent), while four injections would yield six set of values. In one approach, at least two solutions (e.g., 0.5% and 1.5% NaCl solutions) are injected in the targeted luminal organ or vessel. Our studies indicate that an infusion rate of approximately 1 ml/s for a five second interval is sufficient to displace the blood volume and results in a local pressure increase of less than 10 mmHg in the coronary artery. This pressure change depends on the injection rate which should be comparable to the organ flow rate.

In one preferred approach, involving the application of Equations [4] and [5], the vessel is under identical or very similar conditions during the two injections. Hence, variables, such as, for example, the infusion rate, bolus temperature, etc., are similar for the two injections. Typically, a short time interval is to be allowed (1-2 minute period) between the two injections to permit the vessel to return to homeostatic state. This can be determined from the baseline conductance as shown in FIG. 4 or 5. The parallel conductance is preferably the same or very similar during the two injections. In one approach, dextran, albumin or another large molecular weight molecule can be added to the NaCl solutions to maintain the colloid osmotic pressure of the solution to reduce or prevent fluid or ion exchange through the vessel wall.

In one approach, the NaCl solution is heated to body temperature prior to injection since the conductivity of current is temperature dependent. In another approach, the injected bolus is at room temperature, but a temperature correction is made since the conductivity is related to temperature in a linear fashion.

In one approach, a sheath is inserted either through the femoral or carotid artery in the direction of flow. To access the lower anterior descending (LAD) artery, the sheath is inserted through the ascending aorta. For the carotid artery, where the diameter is typically on the order of 5-5.5 mm, a catheter having a diameter of 1.9 mm can be used, as determined from finite element analysis, discussed further below. For the femoral and coronary arteries, where the diameter is typically in the range from 3.5-4 mm, so a catheter of about 0.8 mm diameter would be appropriate. The catheter can be inserted into the femoral, carotid or LAD artery through a sheath appropriate for the particular treatment. Measurements for all three vessels can be made similarly.

Described here are the protocol and results for one exemplary approach that is generally applicable to most arterial vessels. The conductance catheter was inserted through the sheath for a particular vessel of interest. A baseline reading of voltage was continuously recorded. Two containers containing 0.5% and 1.5% NaCl were placed in temperature bath and maintained at 37°. A 5-10 ml injection of 1.5% NaCl was made over a 5 second interval. The detection voltage was continuously recorded over a 10 second interval during the 5 second injection. Several minutes later, a similar volume of 1.5% NaCl solution was injected at a similar rate. The data was again recorded. Matlab was used to analyze the data including filtering with high pass and with low cut off frequency (1200 Hz). The data was displayed using Matlab and the mean of the voltage signal during the passage of each respective solution was recorded. The corresponding currents were also measured to yield the conductance (G=I/V). The conductivity of each solution was calibrated with six different tubes of known CSA at body temperature. A model using Equation [10] was fitted to the data to calculate conductivity C. The analysis was carried out in SPSS using the non-linear regression fit. Given C and G for each of the two injections, an excel sheet file was formatted to calculate the CSA and $G_p$ as per Equations [4] and [5], respectively. These measurements were repeated several times to determine the reproducibility of the technique. The reproducibility of the data was within 5%. Ultrasound (US) was used to measure the diameter of the vessel simultaneous with our conductance measurements. The detection electrodes were visualized with US and the diameter measurements was made at the center of the detection electrodes. The maximum differences between the conductance and US measurements were within 10%.

FIGS. 4A, 4B, 5A and 5B illustrate voltage measurements in the blood stream in the left carotid artery. Here, the data acquisition had a the sampling frequency of 75 KHz, with two channels—the current injected and the detected voltage, respectively. The current injected has a frequency of 5 KH, so the voltage detected, modulated in amplitude by the impedance changing through the bolus injection will have a spectrum in the vicinity of 5 KHz.

Figure 4A:
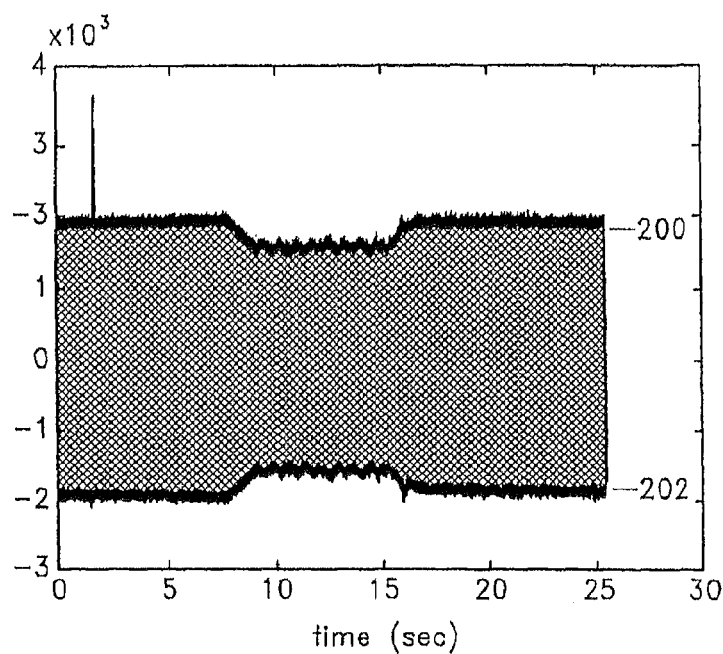
FIG. 4A shows the detected filtered voltage drop as measured in the blood stream before and after injection of 1.5% NaCl solution, according to an embodiment of the present disclosure.
Figure 4B:
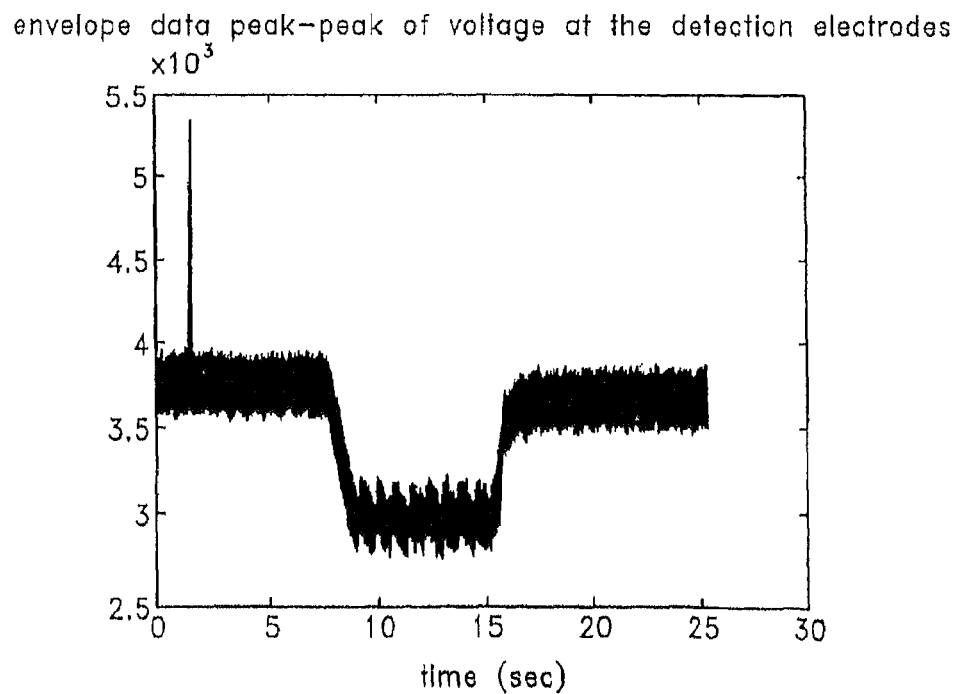
FIG. 4B shows the peak-to-peak envelope of the detected voltage shown in FIG. 4A, according to an embodiment of the present disclosure.
Figure 5A:
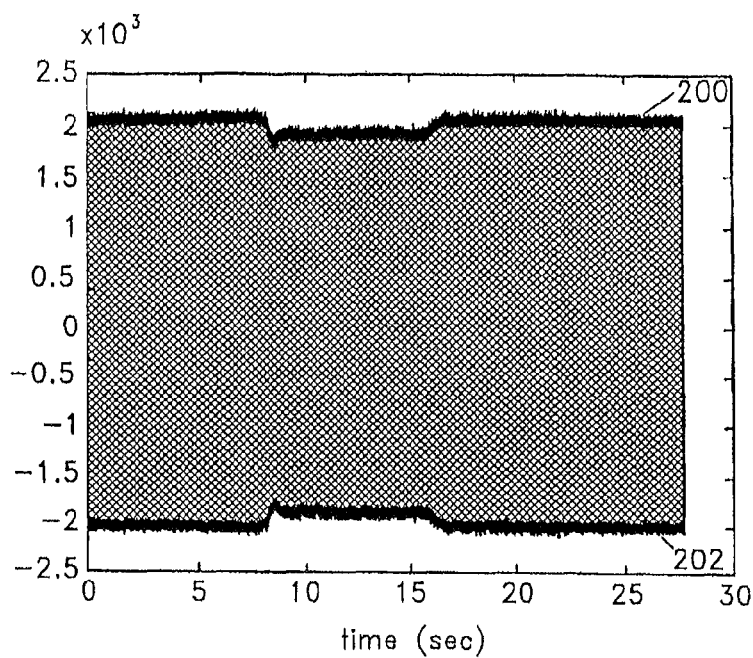
FIG. 5A shows the detected filtered voltage drop as measured in the blood stream before and after injection of 0.5% NaCl solution, according to an embodiment of the present disclosure.
Figure 5B:
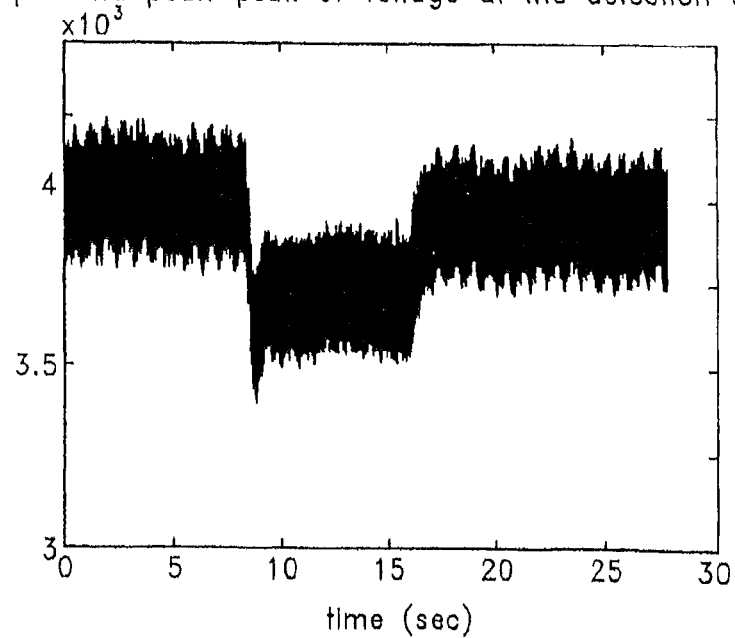
FIG. 5B shows the peak-to-peak envelope of the detected voltage shown in FIG. 5A, according to an embodiment of the present disclosure.

With reference to FIG. 4A there is shown a signal processed with a high pass filter with low cut off frequency (1200 Hz). The top and bottom portions 200, 202 show the peak-to-peak envelope detected voltage which is displayed in FIG. 4B (bottom). The initial 7 seconds correspond to the baseline; i.e., electrodes in the blood stream. The next 7 seconds correspond to an injection of hyper-osmotic NaCl solution (1.5% NaCl). It can be seen that the voltage is decreased implying increase conductance (since the injected current is constant). Once the NaCl solution is washed out, the baseline is recovered as can be seen in the last portion of the FIGS. 4A and 4B. FIGS. 5A and 5B shows similar data corresponding to 0.5% NaCl solutions.

The voltage signals are ideal since the difference between the baseline and the injected solution is apparent and systematic. Furthermore, the pulsation of vessel diameter can be seen in the 0.5% and 1.5% NaCl injections (FIGS. 4 and 5, respectively). This allows determination of the variation of CSA throughout the cardiac cycle as outline above.

The NaCl solution can be injected by hand or by using a mechanical injector to momentarily displace the entire volume of blood or bodily fluid in the vessel segment of interest. The pressure generated by the injection will not only displace the blood in the antegrade direction (in the direction of blood flow) but also in the retrograde direction (momentarily push the blood backwards). In other visceral organs which may be normally collapsed, the NaCl solution will not displace blood as in the vessels but will merely open the organs and create a flow of the fluid. In one approach, after injection of a first solution into the treatment or measurement site, sensors monitor and confirm baseline of conductance prior to injection of a second solution into the treatment site.

The injections described above are preferably repeated at least once to reduce errors associated with the administration of the injections, such as, for example, where the injection does not completely displace the blood or where there is significant mixing with blood. It will be understood that any bifurcation(s) (with branching angle near 90 degrees) near the targeted luminal organ can cause an overestimation of the calculated CSA. Hence, generally the catheter should be slightly retracted or advanced and the measurement repeated. An additional application with multiple detection electrodes or a pull back or push forward during injection will accomplish the same goal. Here, an array of detection electrodes can be used to minimize or eliminate errors that would result from bifurcations or branching in the measurement or treatment site.

In one approach, error due to the eccentric position of the electrode or other imaging device can be reduced by inflation of a balloon on the catheter. The inflation of balloon during measurement will place the electrodes or other imaging device in the center of the vessel away from the wall. In the case of impedance electrodes, the inflation of balloon can be synchronized with the injection of bolus where the balloon inflation would immediately precede the bolus injection. Our results, however, show that the error due to catheter eccentricity is small.

The CSA predicted by Equation [4] corresponds to the area of the vessel or organ external to the catheter (i.e., CSA of vessel minus CSA of catheter). If the conductivity of the NaCl solutions is determined by calibration from Equation [10] with various tubes of known CSA, then the calibration accounts for the dimension of the catheter and the calculated CSA corresponds to that of the total vessel lumen as desired. In one embodiment, the calibration of the CSA measurement system will be performed at 37° C. by applying 100 mmHg in a solid polyphenolenoxide block with holes of known CSA ranging from 7.065 mm$^2$ (3 mm in diameter) to 1017 mm$^2$ (36 in mm). If the conductivity of the solutions is obtained from a conductivity meter independent of the catheter, however, then the CSA of the catheter is generally added to the CSA computed from Equation [4] to give the desired total CSA of the vessel.

The signals are generally non-stationary, nonlinear and stochastic. To deal with non-stationary stochastic functions, one can use a number of methods, such as the Spectrogram, the Wavelet's analysis, the Wigner-Ville distribution, the Evolutionary Spectrum, Modal analysis, or preferably the intrinsic model function (IMF) method. The mean or peak-to-peak values can be systematically determined by the aforementioned signal analysis and used in Equation [4] to compute the GSA.

Figure 6:
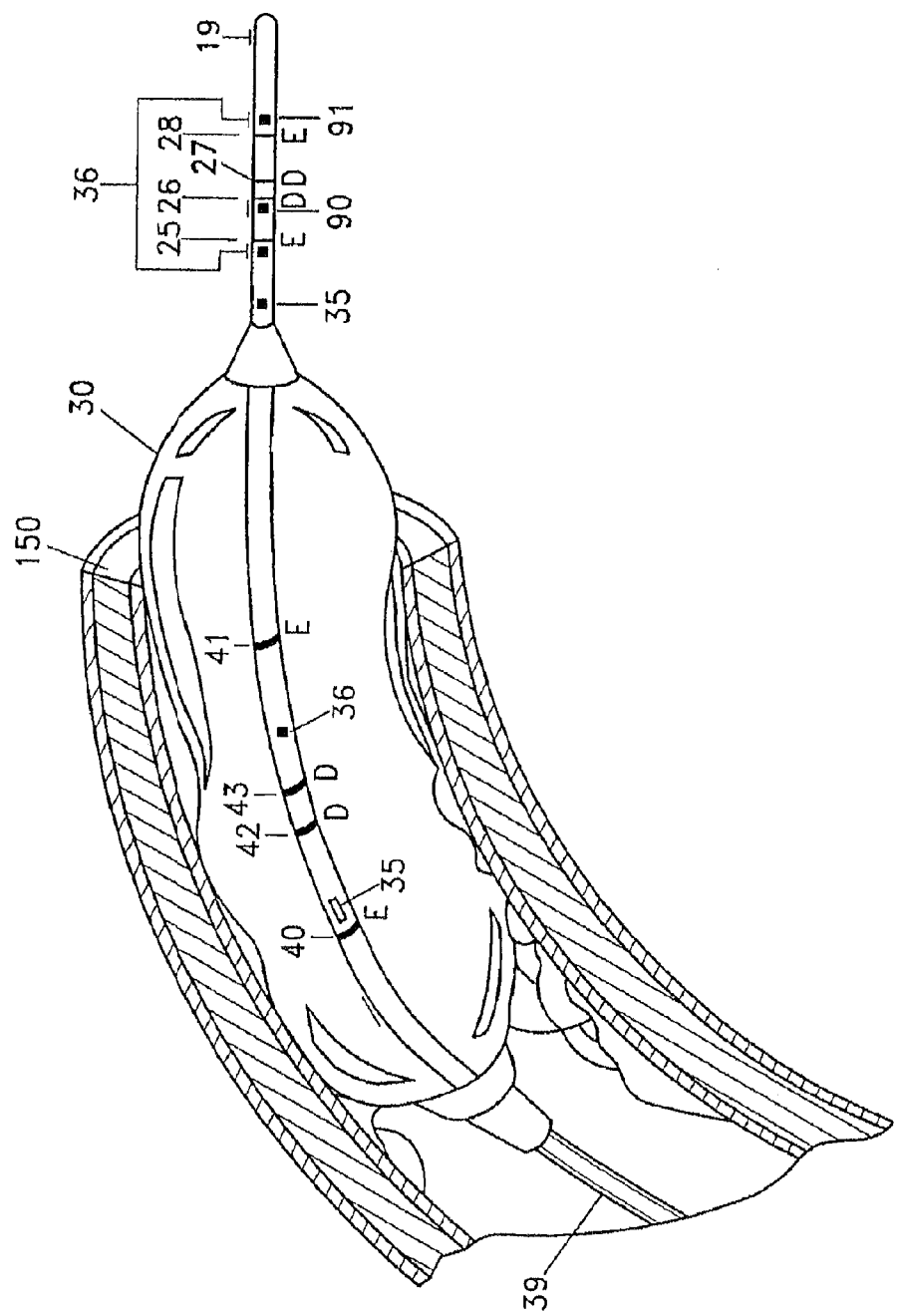
FIG. 6 shows balloon distension of the lumen of the coronary artery, according to an embodiment of the present disclosure.
Figure 7A:
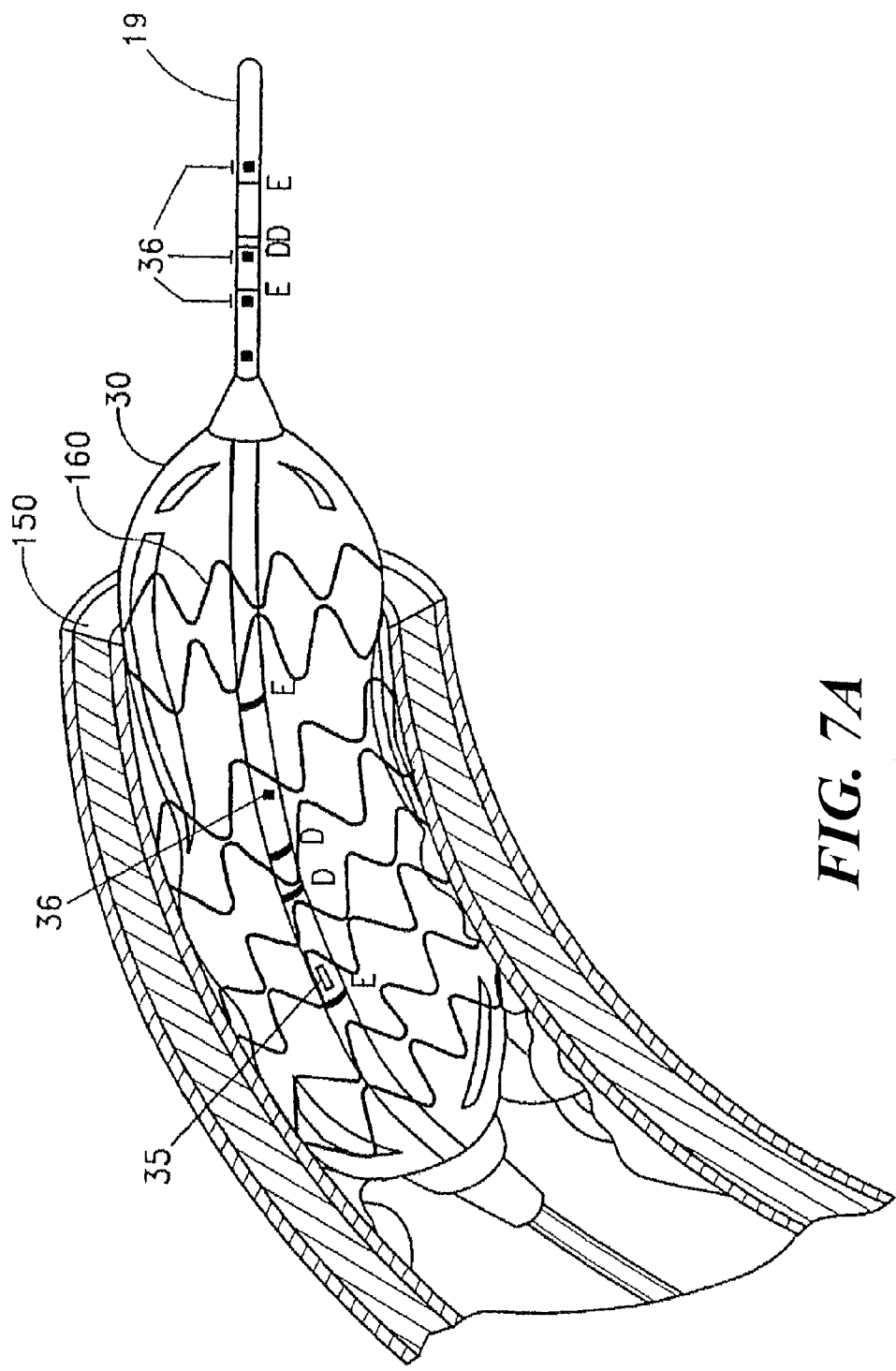
FIG. 7A shows balloon distension of a stent into the lumen of the coronary artery, according to an embodiment of the present disclosure.

Referring to the embodiment shown in FIG. 6, the angioplasty balloon 30 is shown distended within the coronary artery 150 for the treatment of stenosis. As described above with reference to FIG. 1B, a set of excitation electrodes 40, 41 and detection electrodes 42, 43 are located within the angioplasty balloon 30. In another embodiment, shown in FIG. 7A, the angioplasty balloon 30 is used to distend the stent 160 within blood vessel 150.

For valve area determination, it is not generally feasible to displace the entire volume of the heart. Hence, the conductivity of blood is changed by injection of hypertonic NaCl solution into the pulmonary artery which will transiently change the conductivity of blood. If the measured total conductance is plotted versus blood conductivity on a graph, the extrapolated conductance at zero conductivity corresponds to the parallel conductance. In order to ensure that the two inner electrodes are positioned in the plane of the valve annulus (2-3 mm), in one preferred embodiment, the two pressure sensors 36 are advantageously placed immediately proximal and distal to the detection electrodes (1-2 mm above and below, respectively) or several sets of detection electrodes (see, e.g., FIGS. 1D and 1F). The pressure readings will then indicate the position of the detection electrode relative to the desired site of measurement (aortic valve: aortic-ventricular pressure; mitral valve: left ventricular-atrial pressure; tricuspid valve: right atrial-ventricular pressure; pulmonary valve: right ventricular-pulmonary pressure). The parallel conductance at the site of annulus is generally expected to be small since the annulus consists primarily of collagen which has low electrical conductivity. In another application, a pull back or push forward through the heart chamber will show different conductance due to the change in geometry and parallel conductance. This can be established for normal patients which can then be used to diagnose valvular stenosis.

In one approach, for the esophagus or the urethra, the procedures can conveniently be done by swallowing fluids of known conductances into the esophagus and infusion of fluids of known conductances into the urinary bladder followed by voiding the volume. In another approach, fluids can be swallowed or urine voided followed by measurement of the fluid conductances from samples of the fluid. The latter method can be applied to the ureter where a catheter can be advanced up into the ureter and fluids can either be injected from a proximal port on the probe (will also be applicable in the intestines) or urine production can be increased and samples taken distal in the ureter during passage of the bolus or from the urinary bladder.

In one approach, concomitant with measuring the cross-sectional area and or pressure gradient at the treatment or measurement site, a mechanical stimulus is introduced by way of inflating the balloon or by releasing a stent from the catheter, thereby facilitating flow through the stenosed part of the organ. In another approach, concomitant with measuring the cross-sectional area and or pressure gradient at the treatment site, one or more pharmaceutical substances for diagnosis or treatment of stenosis is injected into the treatment site. For example, in one approach, the injected substance can be smooth muscle agonist or antagonist. In yet another approach, concomitant with measuring the cross-sectional area and or pressure gradient at the treatment site, an inflating fluid is released into the treatment site for release of any stenosis or materials causing stenosis in the organ or treatment site.

Again, it will be noted that the methods, systems, and catheters described herein can be applied to any body lumen or treatment site. For example, the methods, systems, and catheters described herein can be applied to any one of the following exemplary bodily hollow systems: the cardiovascular system including the heart; the digestive system; the respiratory system; the reproductive system; and the urogenital tract.

Finite Element Analysis: In one preferred approach, finite element analysis (FEA) is used to verify the validity of Equations [4] and [5]. There are two major considerations for the model definition: geometry and electrical properties. The general Equation governing the electric scalar potential distribution, V, is given by Poisson's Equation as:

$$\nabla \cdot (C \nabla V) = -I \quad [13]$$

where C, I and $\nabla$ are the conductivity, the driving current density and the del operator, respectively. Femlab or any standard finite element packages can be used to compute the nodal voltages using Equation [13]. Once V has been determined, the electric field can be obtained from as $E = -\nabla V$.

The FEA allows the determination of the nature of the field and its alteration in response to different electrode distances, distances between driving electrodes, wall thicknesses and wall conductivities. The percentage of total current in the lumen of the vessel (% I) can be used as an index of both leakage and field homogeneity. Hence, the various geometric and electrical material properties can be varied to obtain the optimum design; i.e., minimize the non-homogeneity of the field. Furthermore, we simulated the experimental procedure by injection of the two solutions of NaCl to verify the accuracy of Equation [4]. Finally, we assessed the effect of presence of electrodes and catheter in the lumen of vessel. The error terms representing the changes in measured conductance due to the attraction of the field to the electrodes and the repulsion of the field from the resistive catheter body were quantified.

We solved the Poisson's Equation for the potential field which takes into account the magnitude of the applied current, the location of the current driving and detection electrodes, and the conductivities and geometrical shapes in the model including the vessel wall and surrounding tissue. This analysis suggest that the following conditions are optimal for the cylindrical model: (1) the placement of detection electrodes equidistant from the excitation electrodes; (2) the distance between the current driving electrodes should be much greater than the distance between the voltage sensing electrodes; and (3) the distance between the detection and excitation electrodes is comparable to the vessel diameter or the diameter of the vessel is small relative to the distance between the driving electrodes. If these conditions are satisfied, the equipotential contours more closely resemble straight lines perpendicular to the axis of the catheter and the voltage drop measured at the wall will be nearly identical to that at the center. Since the curvature of the equipotential contours is inversely related to the homogeneity of the electric field, it is possible to optimize the design to minimize the curvature of the field lines. Consequently, in one preferred approach, one or more of conditions (1)-(3) described above are met to increase the accuracy of the cylindrical model.

Theoretically, it is impossible to ensure a completely homogeneous field given the current leakage through the vessel wall into the surrounding tissue. We found that the iso-potential line is not constant as we move out radially along the vessel as stipulated by the cylindrical model. In one embodiment, we consider a catheter with a radius of 0.55 mm whose detected voltage is shown in FIGS. 7B and 7C for two different NaCl solutions (0.5% and 1.5%, respectively). The origin corresponds to the center of the catheter. The first vertical line 220 represents the inner part of the electrode which is wrapped around the catheter and the second vertical line 221 is the outer part of the electrode in contact with the solution (diameter of electrode is approximately 0.25 mm). The six different curves, top to bottom, correspond to six different vessels with radii of 3.1, 2.7, 2.3, 1.9, 1.5 and 0.55 mm, respectively. It can be seen that a "hill" occurs at the detection electrode 220, 221 followed by a fairly uniform plateau in the vessel lumen followed by an exponential decay into the surrounding tissue. Since the potential difference is measured at the detection electrode 220, 221, our simulation generates the "hill" whose value corresponds to the equivalent potential in the vessel as used in Equation [4]. Hence, for each catheter size, we varied the dimension of the vessel such that Equation [4] is exactly satisfied. Consequently, we obtained the optimum catheter size for a given vessel diameter such that the distributive model satisfies the lumped Equations (Equation [4] and [5]). In this way, we can generate a relationship between vessel diameter and catheter diameter such that the error in the CSA measurement is less than 5%. In one embodiment, different diameter catheters are prepackaged and labeled for optimal use in certain size vessel. For example, for vessel dimension in the range of 4-5 mm, 5-7 mm or 7-10 mm, our analysis shows that the optimum diameter catheters will be in the range of 0.9 1.4, 1.4-2 or 2-4.6 mm, respectively. The clinician can select the appropriate diameter catheter based on the estimated vessel diameter of interest. This decision will be made prior to the procedure and will serve to minimize the error in the determination of lumen CSA.

Devices, Systems, and Methods for Removing Contrast from Luminal Organs

In addition to the foregoing, the disclosure of the present application discloses various devices, systems, and methods for removing contrast from luminal organs. Such devices, systems, and methods provide endovascular detection of contrast medium using impedance sensing to remove contrast during angiography. An aspiration (suction) catheter, for example and referred to below as device 1000, is equipped with impedance sensors and can be inserted into the coronary sinus to allow automated detection and withdrawal of contrast to prevent circulation of contrast and CIN. As referenced herein, "contrast" relates to a contrast medium itself, as well as a bodily fluid, such as blood, and/or a non-native fluid, such as saline, which has mixed with the contrast medium.

Figure 8:
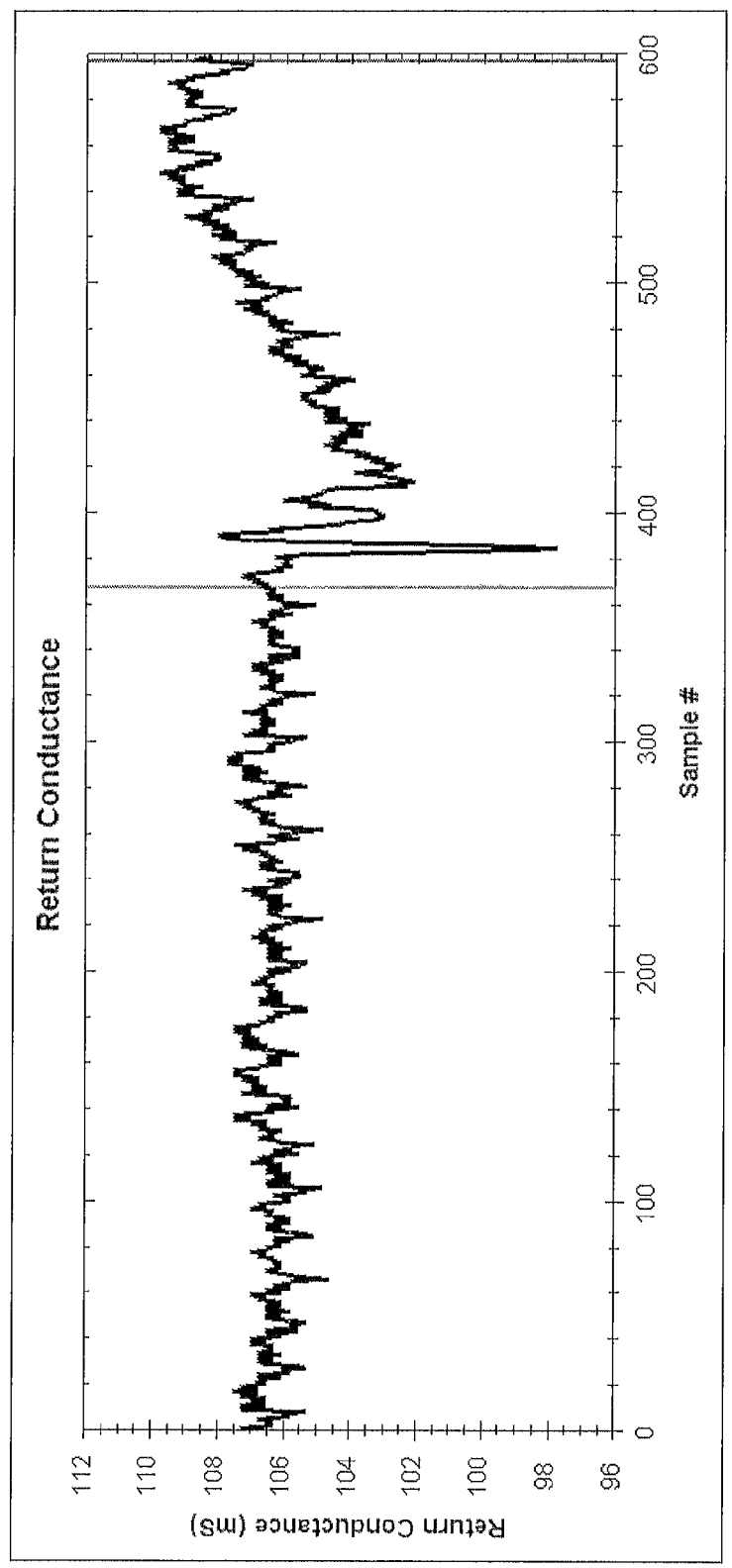
FIG. 8 shows an electrical conductance measurement within a subject showing the change in conductance due to the presence of contrast and saline.

During contrast injection into the coronary arteries to obtain an angiogram, for example, the blood is diluted with iodine which lowers its electrical conductivity (i.e., contrast is non-conductive relative to blood). FIG. 8 shows an example of an electrical conductance measurement (G=I/V) where I is the electrical current and V is the voltage drop measurement along the detection electrodes, which in the tested subject shows a baseline of blood conductance sample readings 0 to about 380. A downward spike can be observed at sample 380 due to iodine injection which substantially reduces the blood conductivity, as iodine is much less conductive than blood as shown in FIG. 8. A saline injection is then followed which shows an increased conductance. The signal to noise ratio is sufficient to trigger aspiration of the contrast at the time of detection and to stop aspiration when contrast is removed.

Catheterization of the coronary sinus can be carried out in accordance with standard procedures. As discussed in further detail below, an exemplary device 1000 of the present disclosure can be introduced through a venous access (femoral vein or axillary vein) into the right atrium and coronary sinus. A balloon coupled to device 1000 may be inflated just prior to injection of contrast, or can be triggered by sensing of contrast just prior to suction, as referenced below.

Figure 9A:
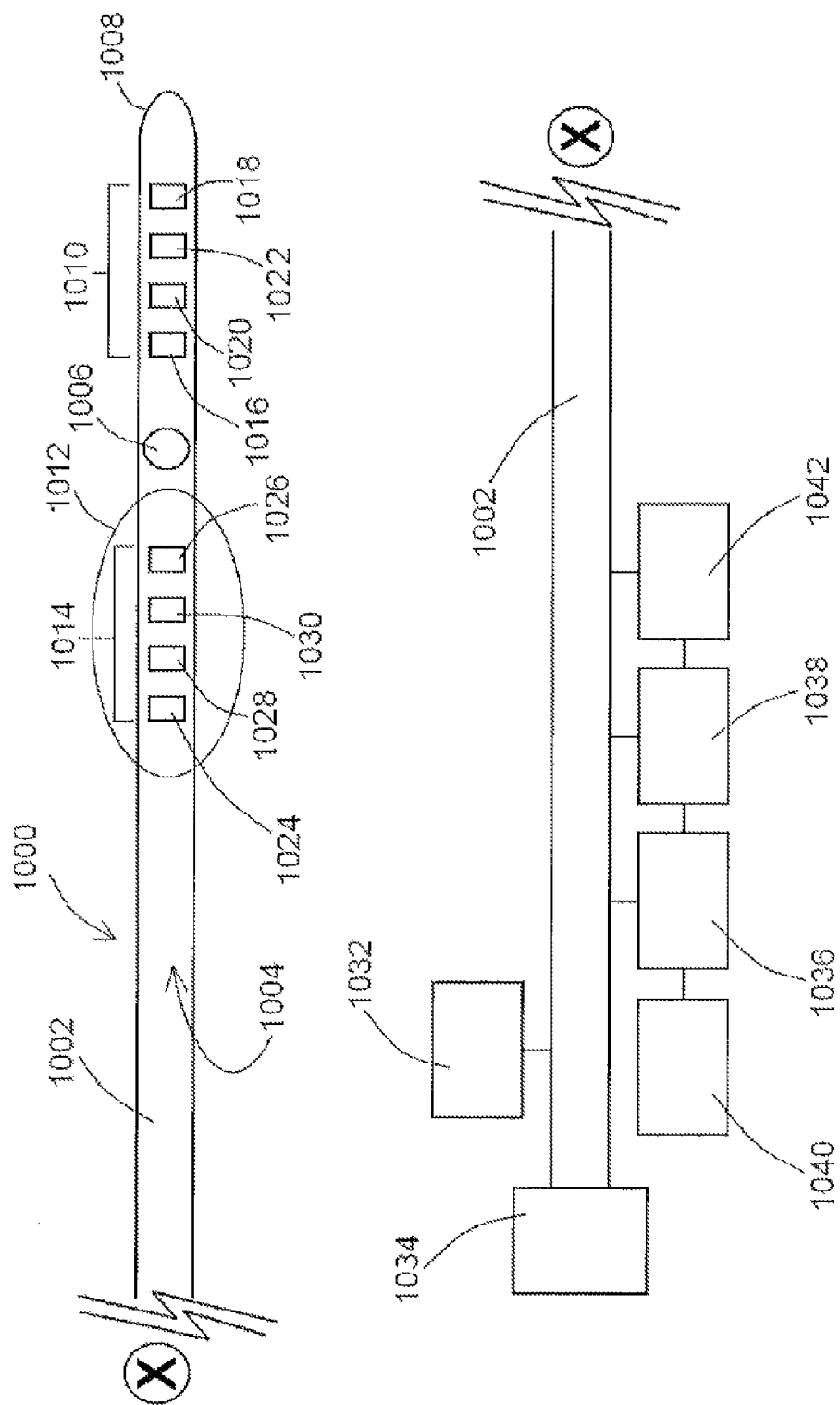
FIGS. 9A and 9B show diagrams of devices for removing contrast from a luminal organ, according to embodiments of the present disclosure.

An exemplary device for removing contrast from a mammalian luminal organ of the present disclosure is shown in FIG. 9A. As shown in FIG. 9A, device 1000 comprises an elongated body 1002 having at least one lumen 1004 extending therethrough, and an aperture 1006 defined along elongated body 1002 proximal or distal to a first detector 1010. In the embodiment shown in FIG. 9A, aperture 1006 is defined along elongated body proximal to detector 1010. In at least one embodiment, device 1000 comprises a catheter. Detector 1010, according to the present disclosure and as shown in FIG. 9A, may be positioned at or near distal end 1008 of elongated body 1002, wherein said first detector 1010 is capable of detecting a contrast present within a mammalian luminal organ (such as, for example, an iodine contrast present within blood within the luminal organ). An exemplary device 1000 of the present disclosure may comprise a coronary sinus catheter having the features described herein.

Figure 9B:
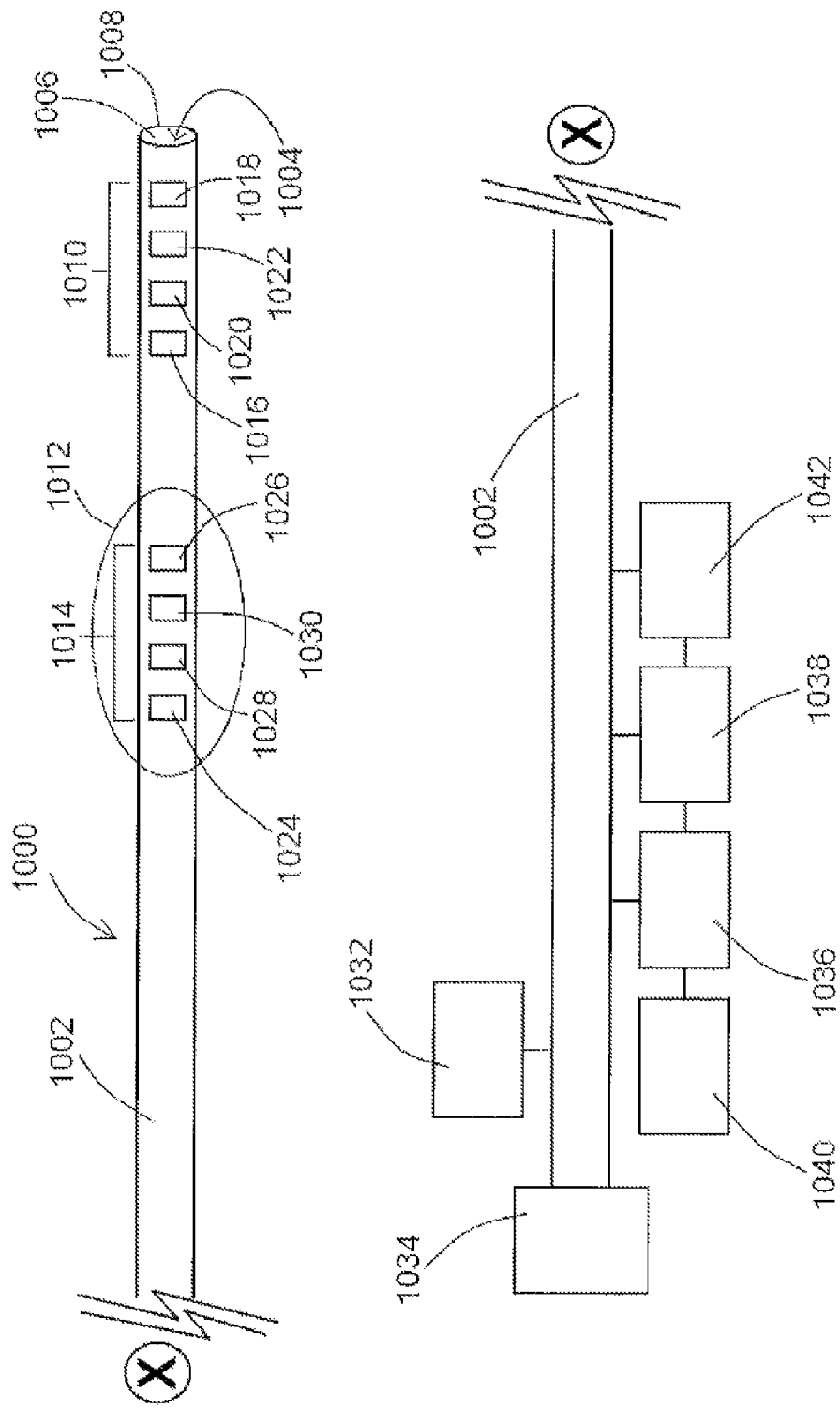

Another exemplary embodiment of a device 1000 of the present disclosure is shown in FIG. 9B. As shown in FIG. 9B, device 1000 comprises an elongated body 1002 having at least one lumen 1004 extending therethrough, wherein lumen 1004 terminates at an aperture 1006 defined at or near a distal end 1008 of elongated body 1002. The exemplary embodiments of devices 1000 shown in FIGS. 9A and 9B are shown in two sections, whereby the two sections actually comprise one overall device 1000 by way of the circled Xs shown in the figures.

Device 1000, as shown in FIGS. 9A and 9B, may also comprise an inflatable balloon 1012 coupled to elongated body 1002. In at least one embodiment, balloon 1012 is coupled to elongated body 1002 proximal to first detector 1010, as shown in FIGS. 9A and 9B. A second detector 1014, positioned inside balloon 1012 along elongated body 1002, may operate to detect balloon 1012 inflation.

In exemplary embodiments of devices 1000, such as shown in FIGS. 9A and 9B, first detector 1010 of devices 1000 comprises a first pair of excitation electrodes 1016, 1018 located on elongated body 1002, and a first pair of detection electrodes 1020, 1022 located on elongated body 1002 in between the first pair of excitation electrodes 1016, 1018. In at least one embodiment, first detector 1010 is capable of obtaining a conductance measurement of a fluid, including contrast for example, present within the mammalian luminal organ at or near device 1000. In at least another embodiment, second detector 1014 of device 1000 comprises a second pair of excitation electrodes 1024, 1026 located on elongated body 1002 and a second pair of detection electrodes 1028, 1030 located on elongated body 1002 in between the first pair of excitation electrodes 1024, 1026, wherein each of electrodes 1024, 1026, 1028, and 1030 are positioned within balloon 1012. In at least one embodiment, second detector 1014 is capable of obtaining a conductance measurement of a fluid within the balloon to determine, for example, balloon cross-sectional area.

In an exemplary embodiment of a device 1000 of the present disclosure, at least one excitation electrode of the first pair of excitation electrodes 1016, 1018 and at least one excitation electrode of the second pair of excitation electrodes 1024, 1026 is/are in communication with a current source 1032 capable of supplying electrical current to said electrodes. In addition, and as shown in FIGS. 9A and 9B, exemplary devices 1000 of the present disclosure may further comprise a data acquisition and processing system 1034 capable of receiving conductance data from the first pair of detection electrodes 1020, 1022 and/or from the second pair of detection electrodes 1028, 1030.

In at least one embodiment, device 1000 comprises a detector 1010 and a balloon 1012 positioned along an elongated body 1002 and at least one lumen 1004 extending therethrough terminating at an aperture 1006 defined at or near a distal end of device 1000. In at least one embodiment, method 1100 further comprises the steps of inflating balloon 1012 to prohibit fluid flow within the luminal organ proximal to balloon 1012 (an exemplary inflation step 1106), removing contrast through aperture 1006 of device 1000 (an exemplary contrast removal step 1108), and ceasing removal of contrast from the luminal organ when a threshold amount of contrast is no longer detected within the luminal organ (an exemplary removal cessation step 1110).

In an exemplary device 1000 of the present disclosure, device 1000 further comprises a suction apparatus 1036 coupled to elongated body 1002, and an electronic module 1038 coupled to the suction apparatus 1036 and first detector 1010, wherein when first detector 1010 detects contrast within the luminal organ, electronic module 1038 activates suction apparatus 1036 to withdraw contrast from the luminal organ. In such an embodiment, for example, withdrawal of contrast from the luminal organ involves operating suction apparatus 1036 to withdraw contrast from the luminal organ, through aperture 1006, and through lumen 1004. In at least one embodiment, suction device 1036 comprises a collector 1040 for collecting contrast.

In at least one embodiment of a device 1000 of the present disclosure, device 1000 further comprises an inflation source 1042 coupled to balloon 1012, and an electronic module 1038 coupled to inflation source 1042 and first detector 1010, wherein when first detector 1010 detects contrast within the luminal organ, electronic module 1038 activates inflation source 1042 to inflate inflatable balloon 1012. In an exemplary embodiment, electronic module 1038 connected to inflation source 1042 is the same electronic module 1038 as connected to suction apparatus 1036, as shown in FIGS. 9A and 9B, but can comprise separate electronic modules 1038 as well. In addition, various components of device 1000, including but not limited to current source 1032, data acquisition and processing system 1034, suction apparatus 1036, electronic module 1038, collector 1040, and inflation source 1042, may be coupled and/or connected to various other components including those listed and, for example, detectors 1010 and 1014 and balloon 1012, via various electrical connections such as wires and/or tubing/conduits to facilitate fluid suction and/or inflation, as appropriate to accomplish the same as referenced herein.

In various embodiments of device 1000, and as referenced generally above, when a fluid is injected through lumen 1004 of elongated body 1002 into balloon 1012, second detector 1014 is capable of obtaining a fluid conductance measurement within balloon 1012, wherein the fluid conductance measurement is useful to determine balloon cross-sectional area. In at least one embodiment, and as shown in FIGS. 9A and 9B, fluid may enter balloon 1012 from lumen 1004 by way of suction/infusion port 1044.

Figure 10:
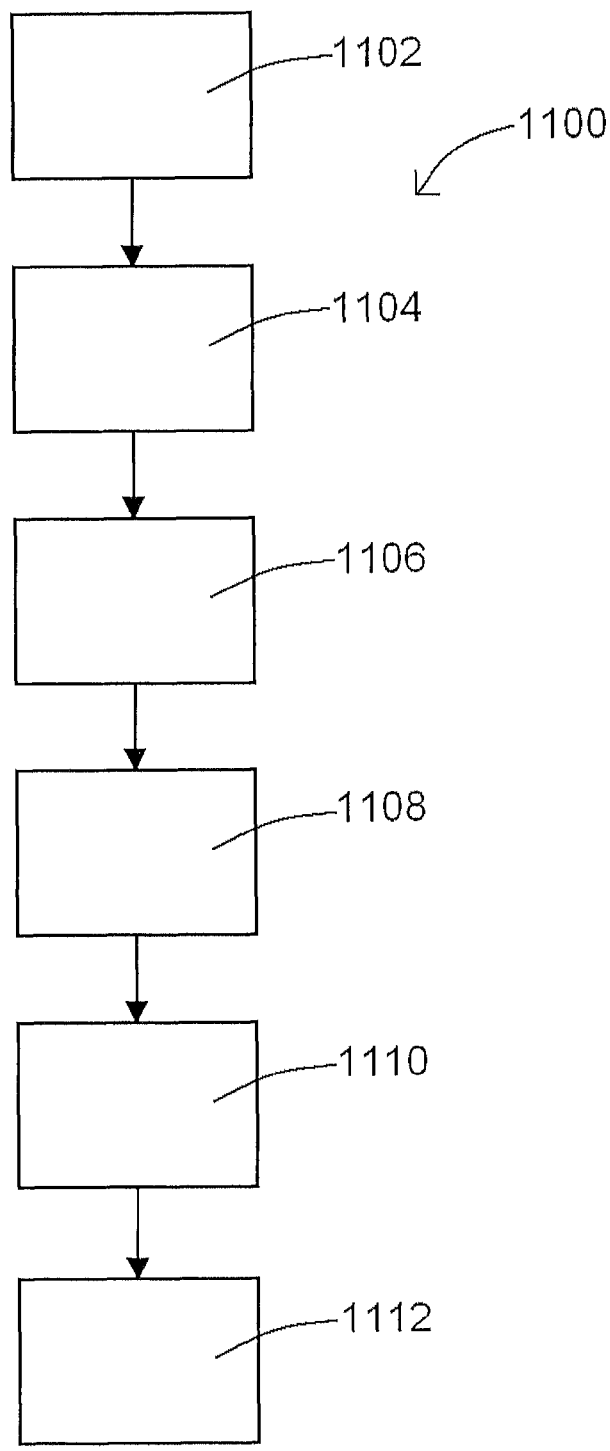
FIG. 10 shows steps of a method for removing contrast from a luminal organ, according to an embodiment of the present disclosure.

Steps of an exemplary method for removing contrast from a mammalian luminal organ of the present disclosure is shown in FIG. 10. As shown in FIG. 10, exemplary method 1100 comprises the steps of inserting at least part of a device 1000 for removing contrast into a luminal organ (an exemplary insertion step 1102) and detecting contrast present within the luminal organ (an exemplary detection step 1104). Insertion step 1102 may be performed to, for example, insert device 1000 into a coronary sinus of a mammalian heart.

In at least one embodiment, device 1000 comprises a detector 1010 and a balloon 1012 positioned along an elongated body 1002 and at least one lumen 1004 extending therethrough terminating at an aperture 1006 defined at or near a distal end of device 100. In at least one embodiment, method 1100 further comprises the steps of inflating balloon 1012 to prohibit fluid flow within the luminal organ proximal to balloon 1012 (an exemplary inflation step 1106), removing contrast through aperture 1006 of device 1000 (an exemplary contrast removal step 1108), and ceasing removal of contrast from the luminal organ when a threshold amount of contrast is no longer detected within the luminal organ (an exemplary removal cessation step 1110).

Balloon inflation step 1106, for example, may be performed by inflating balloon 1012 to a desired size. Such a size may be, for example, identified by way of detector 1014 present within balloon 1012, so that balloon 1012 is inflated so that contrast is prevent from escaping past balloon 1012 and to optimize trapping/removal of contrast without injury to the luminal organ.

In at least one embodiment of a method 1100 of the present disclosure, detection step 1104 is performed using detector 1010 of device 1000. In an exemplary embodiment of method 1100, inflation step 1106 is performed using an inflation source 1042 upon detection of contrast present within the luminal organ. In at least one embodiment, inflation step 1106 and contrast removal step 1108 are performed simultaneously. Contrast removal step 1108 may be performed quite rapidly (in the order of a few seconds, for example), depending on the configuration of lumen 1004 and/or aperture 1006, wherein larger corresponds to quicker removal of contrast, and the amount of suction applied thereto by, for example, suction apparatus 1036. Contrast removal step 1108 may be performed to remove no more than approximately 100 ml of contrast (contrast medium plus blood, for example).

In an exemplary method 1100 for removing contrast from a mammalian luminal organ of the present disclosure, detection step 1104, as shown in FIG. 10, comprises obtaining one or more initial conductance measurements within the luminal organ using detector 1010, the one or more initial conductance measurements obtained without contrast present therein, and then obtaining one or more subsequent conductance measurements within the luminal organ using detector 1010, wherein at least one of the one or more subsequent conductance measurements is a threshold percentage lower than at least one of the one or more initial conductance measurements, which is indicative of the presence of contrast. In such an embodiment, for example, the threshold percentage is at least approximately 10% lower than at least one of the one or more initial conductance measurements.

In at least one exemplary method 1100 of the present disclosure, method 1100 further comprises the step of deflating balloon 1012 to permit fluid flow within the luminal organ proximal to balloon 1012 (an exemplary balloon deflation step 1112), as shown in FIG. 10. In at least one embodiment of method 1000, deflation step 1112 is performed in response to at least a partial conductance measurement recovery. In an exemplary embodiment, the partial conductance measurement recovery is approximately within 5% of at least one of the one or more initial conductance measurements. Deflation step 1112 may be performed by, for example, operating inflation source 1042 in a way to decrease fluid pressure within balloon 1012 to deflate balloon 1012. For example, inflation source 1042 may comprise a syringe used to inject fluid into a balloon 1012, and removal of fluid from balloon 1012 to deflate balloon 1012 could be performed by withdrawing fluid from balloon 1012 using the same syringe.

Figure 11:
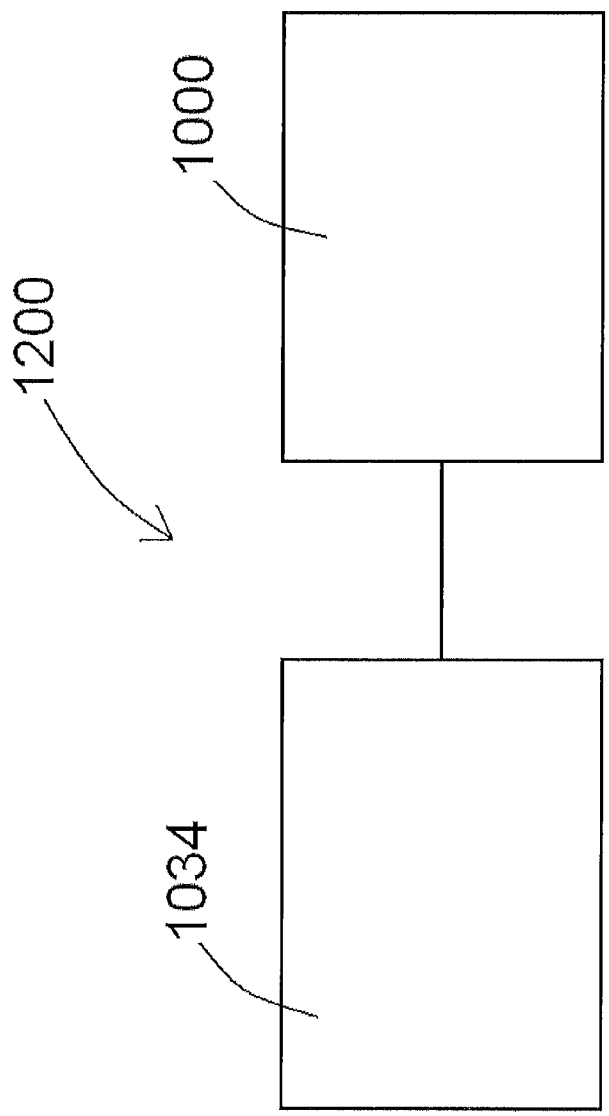
FIG. 11 shows a diagram of a system for removing contrast from a luminal organ, according to an embodiment of the present disclosure.

Exemplary systems 1200 for removing contrast from luminal organs of the present disclosure may comprise exemplary devices 1000 with one or more components/features present. For example, an exemplary device 1000 may comprise an elongated body 1002 with a lumen therethrough 1004 terminating at an aperture 1006, as well as a detector 1010 and a balloon 1012 coupled thereto. An exemplary system 1200 may comprise that same embodiment of a device 1000, for example, along with a current source 1032, a data acquisition and processing system 1034, a suction apparatus 1036, an electronic module 1038, a collector 1040, and/or an inflation source 1042. Devices 1000 and systems 1200 of the present disclosure, depending on configuration, may be one in the same, and any description regarding components and/or features of devices 1000 of the present disclosure also apply to various systems 1200 of the present disclosure. By way of example, and as shown in the block diagram of FIG. 11, an exemplary system of the present disclosure comprises a device 1000 coupled a data acquisition and processing system 1034, but is not limited to such a configuration. In addition, said components/features may be described using more than one reference number; therefore, corresponding descriptions as to such components/features among various devices, systems, and methods are intended to apply to each component/feature. For example, excitation electrodes 40 and 41 may be one in the same as excitation electrodes 1016 and 1018, and description in connection with one is intended to apply to the other.

Figure 12:
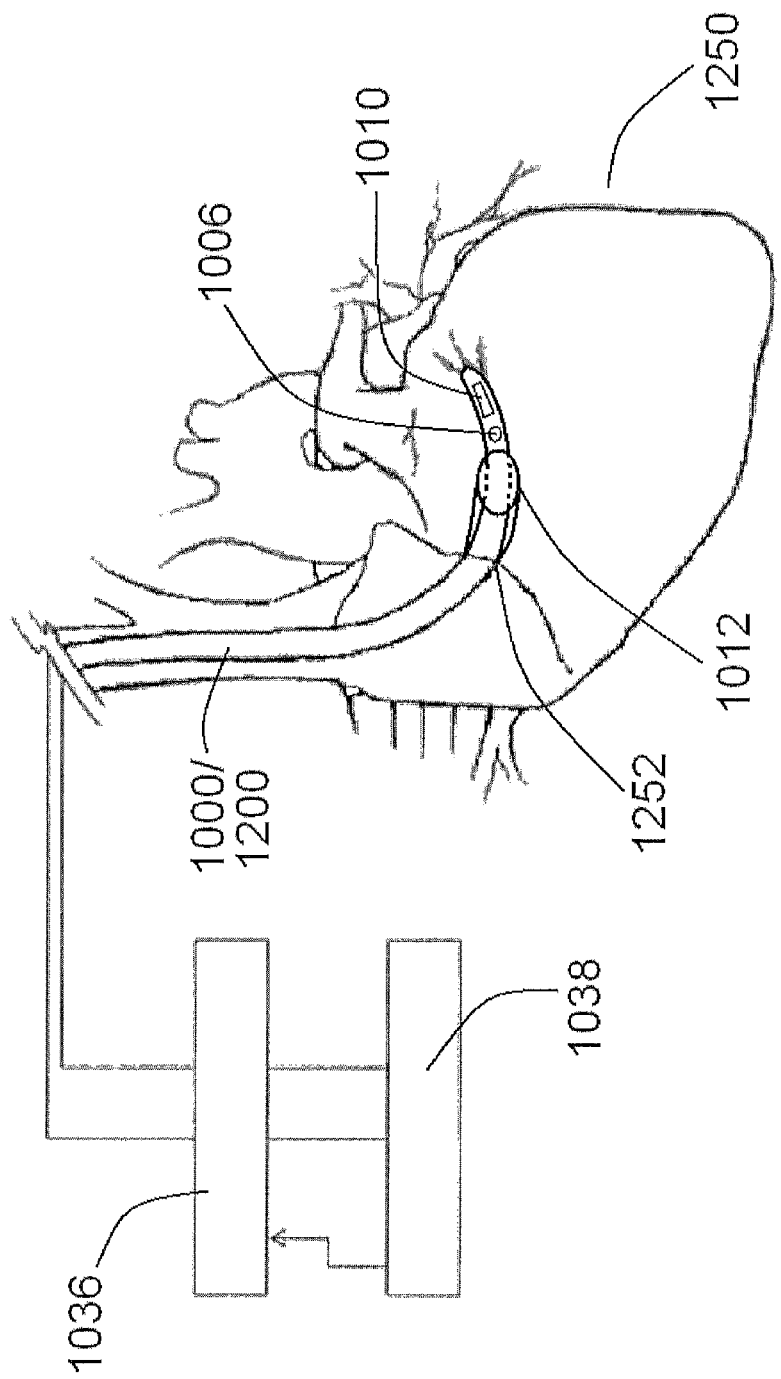
FIG. 12 shows a device/system for removing contrast from a luminal organ present within a heart, according to an embodiment of the present disclosure.

An exemplary embodiment of a device 1000/system 1200 of the present disclosure positioned within a heart 1250 (an exemplary luminal organ) is shown in FIG. 12. As shown in FIG. 12, device 1000/system 1200 comprises an aperture 1006 proximal to a detector 1010 capable of obtaining real-time conductance changes as shown in FIG. 8. The exemplary device 1000/system 1200 shown in FIG. 12 is shown positioned within a coronary sinus 1252, whereby a balloon 1012 can be inflated to occlude coronary sinus 1252 during suction of contrast. Device 1000/system 1200, as shown in FIG. 12, is also connected to (or further comprises) a suction apparatus 1036 which can be triggered by an electronic module 1038 that senses the level of contrast to permit only removal of blood containing the contrast.

The various devices 1000, systems 1200, and methods 1100 for removing contrast from a luminal organ of the present disclosure have a number of advantages over other means for removing contrast which may be used prior to this disclosure. For example, the devices 1000 and systems 1200 of the present disclosure provide active monitoring and detection, whereby, in at least one embodiment, such devices 1000 and systems 1200 may be activated/triggered when a detector 1010 detects contrast. Such devices 1000 and/or systems 1200 do not require constant monitoring by a physician, for example, as they can be configured as referenced herein to operate to remove contrast when detected, which can be in the order of a few seconds. Such devices 1000, systems 1200, and methods 1100 also minimize the amount of blood removed while maximizing the amount of contrast removed as referenced herein, thus reducing or eliminating the risk of contrast-induced nephropathy.

Again, it is noted that the various devices, systems, and methods described herein can be applied to any body lumen or treatment site. For example, the devices, systems, and methods described herein can be applied to any one of the following exemplary bodily hollow organs: the cardiovascular system including the heart, the digestive system, the respiratory system, the reproductive system, and the urogenital tract.

While various embodiments of devices, systems, and methods for removing contrast from luminal organs have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

I claim:

1. A method of removing contrast from a luminal organ, the method comprising the steps of:
   inserting at least part of a device for removing contrast into a mammalian luminal organ, the device having a first detector and a balloon positioned along an elongated body, at least one lumen extending therethrough, and an aperture defined along the elongated body;
   detecting contrast present within the mammalian luminal organ by obtaining one or more initial conductance measurements within the mammalian luminal organ using the first detector, the one or more initial conductance measurements obtained without contrast present therein, and obtaining one or subsequent conductance measurements within the mammalian luminal organ using the first detector, wherein at least one of the one or more subsequent conductance measurements is a threshold percentage lower than at least one of the one or more initial conductance measurements;
   inflating the balloon to prohibit fluid flow within the mammalian luminal organ proximal to the balloon;
   removing contrast through the aperture of the device; and
   ceasing removal of contrast from the mammalian luminal organ when a threshold amount of contrast is no longer detected within the mammalian luminal organ.

2. The method of claim 1, wherein the step of detecting contrast is performed using the first detector of the device.

3. The method of claim 1, wherein the step of inflating the balloon is performed using an inflation source upon detection of contrast present within the mammalian luminal organ.

4. The method of claim 1, wherein the steps of inflating the balloon and removing contrast are performed simultaneously.

5. The method of claim 1, wherein the step of inflating the balloon is performed by inflating the balloon to a desired size.

6. The method of claim 5, wherein the desired size corresponds to a size detected by a second detector positioned along the elongated body within the balloon.

7. The method of claim 5, wherein the desired size corresponds to a size so that contrast is prevented from escaping past the balloon but does not cause injury to the mammalian luminal organ.

8. The method of claim 1, wherein the threshold percentage is at least approximately 10% lower than at least one of the one or more initial conductance measurements.

9. The method of claim 1, further comprising the step of:
   deflating the balloon to permit fluid flow within the mammalian luminal organ proximal to the balloon.

10. The method of claim 9, wherein the deflation step is performed in response to at least a partial conductance measurement recovery.

11. The method of claim 10, wherein the partial conductance measurement recovery is approximately within 5% of at least one of the one or more initial conductance measurements.

12. The method of claim 1, wherein said method is performed to reduce or eliminate a risk of contrast-induced nephropathy.

13. The method of claim 1, wherein the mammalian luminal organ comprises a heart, and wherein the device is inserted within a coronary sinus of the heart.

14. The method of claim 1, wherein the step of removing contrast removes no more than approximately 100 ml of contrast.

15. A method for removing contrast from a mammalian luminal organ, the method comprising the steps of:
   inserting at least part of a device for removing contrast into a mammalian luminal organ, the device having a first detector and a balloon positioned along an elongated body, at least one lumen extending therethrough, and an aperture defined along the elongated body:
   detecting contrast present within the mammalian luminal organ;
   inflating the balloon to prohibit fluid flow within the mammalian luminal organ proximal to the balloon;
   removing contrast through the aperture of the device;
   ceasing removal of contrast from the mammalian luminal organ when a threshold amount of contrast is no longer detected within the mammalian luminal organ; and
   deflating the balloon to permit fluid flow within the mammalian luminal organ proximal to the balloon, in response to at least a partial conductance measurement recovery.

16. The method of claim 15, wherein the step of detecting contrast is performed using the first detector of the device.

17. The method of claim 15, wherein the step of inflating the balloon is performed using an inflation source upon detection of contrast present within the mammalian luminal organ.

18. The method of claim 15, wherein the steps of inflating the balloon and removing contrast are performed simultaneously.

19. The method of claim 15, wherein the step of inflating the balloon is performed by inflating the balloon to a desired size.

20. The method of claim 15, wherein the partial conductance measurement recovery is approximately within 5% of at least one of the one or more initial conductance measurements.

21. The method of claim 15, wherein said method is performed to reduce or eliminate a risk of contrast-induced nephropathy.

22. A method for removing contrast from a mammalian luminal organ, the method comprising the steps of
   inserting at least part of a detection device for removing contrast into a mammalian luminal organ, the detection device having a balloon positioned along an elongated body, at least one lumen extending therethrough, and an aperture defined along the elongated body;
   detecting contrast within the mammalian luminal organ using the detection device by obtaining at least one second conductance measurement within the mammalian luminal organ that is/are a threshold percentage lower than at least one first conductance measurement obtained within the mammalian luminal organ, the threshold percentage indicative of contrast within the mammalian luminal organ;
   inflating the balloon to prohibit fluid flow within the mammalian luminal organ proximal to the balloon;
   removing contrast through the aperture of the detection device; and ceasing removal of contrast from the mammalian luminal organ when a threshold amount of contrast is no longer detected within the mammalian luminal organ.

23. The method of claim 22, wherein the step of detecting contrast is performed using the detection device comprising a detector comprising a pair of detection electrodes positioned in between a pair of excitation electrodes, the pair of excitation electrodes operable to generate an electric field detectable by the pair of detection electrodes.

24. The method of claim 22, wherein the step of inflating the balloon is performed using an inflation source upon detection of contrast present within the mammalian luminal organ.

25. The method of claim 22, wherein the steps of inflating the balloon and removing contrast are performed simultaneously.

26. The method of claim 22, wherein said method is performed to reduce or eliminate a risk of contrast-induced nephropathy.

27. The method of claim 22, wherein the mammalian luminal organ comprises a heart, and wherein the detection device is inserted within a coronary sinus of the heart.

* * * * *